US009522909B2

(12) United States Patent
Boisbrun et al.

(10) Patent No.: US 9,522,909 B2
(45) Date of Patent: Dec. 20, 2016

(54) THIAZOLIDINEDIONE DERIVATIVES, PREPARATION THEREOF AND USE THEREOF IN CANCER TREATMENT

(71) Applicants: Michel Boisbrun, Pulnoy (FR); Yves Chapleur, Nancy (FR); Andrea Bordessa, Gravedona Ed Uniti (IT); Stephane Flament, Vandoeuvre-les-nancy (FR); Isabelle Grillier-Vuissoz, Villiers-les-Nancy (FR); Sandra Kuntz, Crantenoy (FR)

(72) Inventors: Michel Boisbrun, Pulnoy (FR); Yves Chapleur, Nancy (FR); Andrea Bordessa, Gravedona Ed Uniti (IT); Stephane Flament, Vandoeuvre-les-nancy (FR); Isabelle Grillier-Vuissoz, Villiers-les-Nancy (FR); Sandra Kuntz, Crantenoy (FR)

(73) Assignees: UNIVERSITE DE LORRAINE, Nancy (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 14/374,030

(22) PCT Filed: Jan. 25, 2013

(86) PCT No.: PCT/EP2013/051514
§ 371 (c)(1),
(2) Date: Jul. 23, 2014

(87) PCT Pub. No.: WO2013/110796
PCT Pub. Date: Aug. 1, 2013

(65) Prior Publication Data
US 2014/0364465 A1 Dec. 11, 2014

(30) Foreign Application Priority Data

Jan. 26, 2012 (FR) ..................................... 12 50753

(51) Int. Cl.
| | | |
|---|---|---|
| C07D 417/12 | (2006.01) | |
| C07D 417/14 | (2006.01) | |
| C07D 311/66 | (2006.01) | |
| C07D 417/06 | (2006.01) | |
| C07D 277/34 | (2006.01) | |
| C07D 311/74 | (2006.01) | |

(52) U.S. Cl.
CPC ........... *C07D 417/14* (2013.01); *C07D 277/34* (2013.01); *C07D 311/66* (2013.01); *C07D 311/74* (2013.01); *C07D 417/06* (2013.01); *C07D 417/12* (2013.01)

(58) Field of Classification Search
CPC ............................. C07D 417/12; C07D 417/14
See application file for complete search history.

(56) References Cited

U.S. PATENT DOCUMENTS

| 5,387,596 A * | 2/1995 | Takebayashi ........ C07D 417/12 514/233.5 |
| 7,615,650 B2 * | 11/2009 | Tanaka et al. ................ 549/405 |
| 2006/0141591 A1* | 6/2006 | Kyuuko et al. ............... 435/125 |
| 2009/0291992 A1* | 11/2009 | Chen .................... C07D 277/34 514/369 |

FOREIGN PATENT DOCUMENTS

| EP | 0 454 501 A2 | 10/1991 |
| JP | 8 286293 A | 11/1996 |
| JP | 2007063444 A | 3/2007 |
| WO | 2009/105621 A1 | 8/2009 |

OTHER PUBLICATIONS

Chemical Abstracts Registry No. 364595-36-8, indexed in the Registry file on STN CAS Online Oct. 25, 2001.*
Chemical Abstracts Registry No. 365977-37-3, indexed in the Registry file on STN CAS Online Nov. 1, 2001.*
Chemical Abstracts Registry No. 365985-83-7, indexed in the Registry file on STN CAS Online Nov. 1, 2001.*
Chemical Abstracts Registry No. 367461-29-8, indexed in the Registry file on STN CAS Online Nov. 7, 2001.*
Chemical Abstracts Registry No. 438484-68-5, indexed in the Registry file on STN CAS Online Jul. 12, 2002.*
Jih-Hwa Guh et al.: "Development of Novel Adenosine Monophosphate-Activated Protein Kinase Activators", Journal of Medicinal Chemistry, vol. 53, No. 6, Mar. 25, 2010 (Mar. 25, 2010), pp. 2552-2561, XP055038069, ISSN: 0022-2623, 001: 10.1021/jm901773d cited in the application the whole document, compound 43.
Stephane Salamone et al. : "Synthesis of new troglitazone derivatives: Anti-proliferative activity in breast cancer cell lines and preliminary toxicological study", European Journal of Medicinal Chemistry. vol. 51. May 1, 2012 (May 1, 2012). pp. 206-215. XP055038171, ISSN: 0223-5234. DOI: 10.1016/j.jmech.2012.02.044 the whole document schema 1; tableau 1.
Dasheng Wang et al.: "Development of a Novel Class of Glucose Transporter Inhibitors", Journal of Medicinal Chemistry, vol. 55. No. 8. Apr. 26, 2012 (Apr. 26, 2012) pp. 3827-3836. XP055053795, ISSN: 0022-2623. DOI: 10.1021/jm300015m the whole document figures 1.2; compounds 11.13-15.
Jian Yang et al.: "Pharmacological Exploitation of the Peroxisome Proliferator-Activated Receptor γ Agonist Ciglitazone to Develop a Novel Class of Androgen Receptor-Ablative Agents", Received Sep. 25, 2007, J. Med. Chem. 2008, 51, 2100-2107.

(Continued)

*Primary Examiner* — Laura L. Stockton
(74) *Attorney, Agent, or Firm* — Young & Thompson

(57) ABSTRACT

The present invention relates to thiazolidinedione derivatives, to the processes for preparing same and to the therapeutic use thereof for preventing or treating cancer, and more specifically breast cancer. These compounds are of formula (I) and exhibit, at a concentration of 100 μM, a hepatocyte viability preferably greater than 60%, preferably greater than 80% and more preferentially greater than 85%.

10 Claims, No Drawings

(56) References Cited

OTHER PUBLICATIONS

Youfu Luo et al.: "Discovery of (Z)-5-(4-Methoxybenzylidene)thiazolidine-2,4-dione, a Readily Available and Orally Active Glitazone for the Treatment of Concanavalin A-Induced Acute Liver Injury of BALB/c Mice", J. Med. Chem. 2010, 53, 273-281.
Jui-Wen Huang et al.: "Development of Small-Molecule Cyclin D1-Ablative Agents", J. Med. Chem. 2006, 49, 4684-4689, Received Jan. 17, 2006, Novel Cyclin D1-Ablative Agents.
Lucie Guetzoyan et al.: "In vitro efficiency of new acridyl derivatives against Plasmodium falciparum", Bioorganic & Medicinal Chemistry 15 (2007) 3278-3289, revised Feb. 2, 2007; accepted Feb. 9, 2007.
Elias A. Couladouros et al. "A Short and Convenient Chemical Route to Optically Pure 2-Methyl Chromanmethanols. Total Asymmetric Synthesis of â-, ç-, and ä-Tocotrienols", Received Mar. 15, 2007, Chemistry Laboratories, Agricultural University of Athens, Iera Odos 75, GR 118 55 Athens, Greece,J. Org. Chem. 2007, 72, 6735-6741.
FR Search Report, dated Sep. 19, 2012, from corresponding FR application.
International Search Report, dated Jul. 11, 2013, from corresponding PCT application.

\* cited by examiner

THIAZOLIDINEDIONE DERIVATIVES, PREPARATION THEREOF AND USE THEREOF IN CANCER TREATMENT

TECHNICAL FIELD

The present invention relates to thiazolidinedione derivatives, to their preparation methods and their use in therapeutics. More particularly, the present invention relates to novel compounds derived from thiazolidinedione for therapeutic use in preventing and treating cancers, and more specifically breast cancers.

STATE OF THE ART

Derivatives of thiazolidinediones or glitazones, such as troglitazone (TGZ), rosiglitazone (RGZ) and the pioglitazone (PGZ) were used in human therapy for the treatment of diabetes of type 2. Their activity was described as being due to their activating PPARγ property. These receptors for which three sub-types (α, γ, δ) exist, are located in cell nuclei and are intimately associated with the DNA. Their activation by endogenous compounds (fatty acids, prostaglandins) or synthetic compounds (molecules of the family of glitazones or other more recent compounds) induces complex modulation of the expression of certain genes resulting in lowering of glycemia and resistance to insulin.

Later on, antiproliferative properties of certain glitazones and in particular of TGZ were discovered. The latter was even the object of clinical trials of phase II within the scope of breast cancer. The route(s) through which troglitazone exerts its antiproliferative activity are still in discussion, but more and more studies suggest that they would at least partly be independent of PPARγ.

It is mentioned that healthy cells do not seem to react to these compounds in the same way as cancer cells, which is in favor of their clinical use.

A negative point has prevented for a long time the use of TGZ for its anti-cancer properties: this molecule induces substantial hepatic disorders in a non-predictable way in certain persons. This is not the case in rodents and thus the molecule was able to pass the filter of pre-clinical trials. This difference between animals and humans seems due to differences in metabolization and subsequent developments of similar molecules will be ensured, provided that their toxicity on human cells is well investigated.

This hepatic toxicity of TGZ has led to its withdrawal from the market in 2000 while it had been used since 1997 for its anti-diabetic properties. RGZ was withdrawn from the market in autumn 2010 for heart toxicity reasons. Also PGZ was withdrawn from the French market since it would induce an increased risk of development of cancer of the bladder.

It is therefore necessary to optimize the anti-proliferative properties of TGZ, while attempting to reduce the hepatotoxicity thereof.

Δ2TGZ, a similar molecule but including an additional double bond has been reported in the literature as being without any PPARγ activity but having anti-proliferative properties comparable or even slightly superior to those of TGZ. Derivatives of this molecule were prepared by Chen et al. (J.-W. Huang, C.-W. Shiau, J. Yang, D.-S. Wang, H.-C. Chiu, C.-Y. Chen, C.-S. Chen, J. Med. Chem. 49 (2006) 4684-4689), who thereby obtained compounds for which the anti-proliferative activity is of the order of one micromolar. Other derivatives have been described later on in the literature (J. Yang, S. Wei, D.-S. Wang, Y.-C. Wang, S. K. Kulp, C.-S. Chen, J. Med. Chem. 51 (2008) 2100-2107; J.-H. Guh, W.-L. Chang, J. Yang, S.-L. Lee, S. Wei, D. Wang, S. K. Kulp, C.-S. Che, J. Med. Chem. 53 (2010) 2552-2561) and in international application WO 2009/105621. However, these compounds have some hepatic toxicity and therefore cannot be used.

It is therefore necessary to propose novel molecules derived from thiazolidinediones having low hepatic toxicity, while having an anti-proliferative activity superior to that of TGZ.

DISCLOSURE OF THE INVENTION

For this purpose, and according to the present invention, novel compounds of formula (I) are proposed

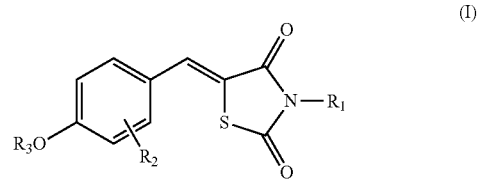

having, at a concentration of 100 μM, hepatocyte viability preferably greater than 60%, preferably greater than 80%, and more preferentially greater than 85%, and such that:
when $R_1$ is H, then
$R_3$ is a group

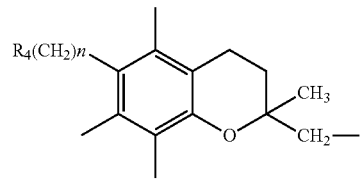

where n is greater than 1 and $R_4$ is selected from the group comprising H, OH, COOR, NRR', NHCOOR", NHM groups, R and R' being selected from H, an alkyl group and a benzyl group, R" being a group selected from an alkyl group and a benzyl group and M being a fluorescent group, and
$R_2$ is selected from the group comprising hydrogen, halo, amino, methoxy, ethoxy, nitro, phenyl, dialkyl, dihalo, trifluoromethyl, hydroxyl group;
when $R_1$ is selected from the group comprising alkyl, benzyl, —$(CH_2)_m$—CH=CH-Φ,

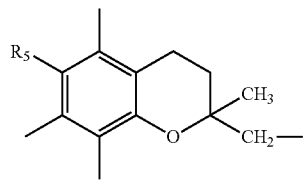

group where m is greater than or equal to 1, $R_5$ is selected from the group comprising H, OH, COOH, COOR, OCOOR, $(CH_2)_pR_9$, $O(CH_2)_pR_9$, $OCO(CH_2)_pR_9$, where p is greater than 1, preferably greater than or equal to 2, $R_9$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, then, $R_3$ is a group selected from the group comprising H,

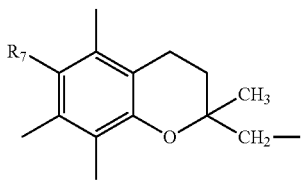

where $R_7$ is selected from the group comprising H, OH, COOH, COOR, OCOOR, $(CH2)qR_8$, $O(CH2)qR_8$, $OCO(CH2)qR_8$, where q is greater than or equal to 1, preferably greater than or equal to 2, $R_8$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, and $R_2$ is selected from the group comprising hydrogen, amino, methoxy, ethoxy, nitro, phenyl, di-alkyl, hydroxyl group, when $R_1$ is selected from alkyl or benzyl group, except for the compounds for which:
$R_1$ is butyl, $R_2$ is methoxy, $R_3$ is H;
$R_1$ is ethyl, $R_2$ is H, $R_3$ is H;
$R_1$ is methyl, $R_2$ is OH, $R_3$ is H;

$R_2$ is selected from the group comprising hydrogen, halo, amino, methoxy, ethoxy, nitro, phenyl, di-alkyl, di-halo, trifluoromethyl, hydroxyl group, when $R_1$ is selected from the group comprising $-(CH_2)_m-CH=CH-\Phi$, and

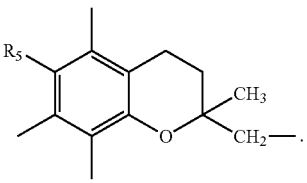

EMBODIMENT(S) OF THE INVENTION

According to another definition of the invention, novel compounds of formula (I) are proposed

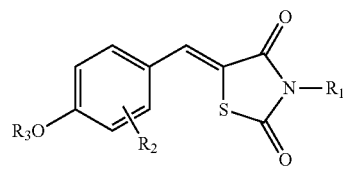

(I)

having, at a concentration of 100 μm, a hepatocyte viability preferably greater than 60%, preferably greater than 80%, and more preferentially greater than 85%, and such that:

when $R_1$ is H, then
$R_3$ is a group

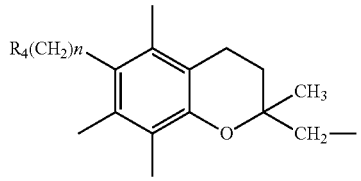

where m is greater than 1 and $R_4$ is selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, and $R_2$ is selected from the group comprising hydrogen, halo, amino, methoxy, ethoxy, nitro, phenyl, dialkyl, dihalo, trifluoromethyl, hydroxyl group;

when $R_1$ is selected from the group comprising alkyl, benzyl, $-(CH_2)_m-CH=CH-\Phi$,

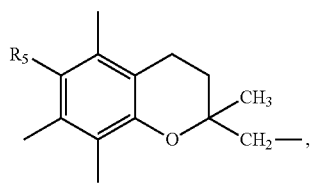

group where m is greater than or equal to 1, $R_5$ is selected from the group comprising H, OH, COOH, COOR, OCOOR, $(CH_2)_pR_9$, $O(CH_2)_pR_9$, $OCO(CH_2)_pR_9$, where p is greater than 1, preferably greater than or equal to 2, $R_9$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, $R_3$ is a group selected from the group comprising H,

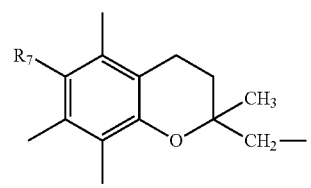

where $R_7$ is selected from the group comprising H, OH, COOH, COOR, OCOOR, $(CH_2)_qR_8$, $O(CH_2)_qR_8$, $OCO(CH_2)_qR_8$, where q is greater than or equal to 1, preferably greater than or equal to 2, $R_8$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, and $R_2$ is selected from the group comprising hydrogen, amino, methoxy, ethoxy, nitro, phenyl, di-alkyl, hydroxyl group, when $R_1$ is selected from alkyl or benzyl groups, provided that:

when $R_1$ is butyl and $R_2$ is methoxy, $R_3$ is

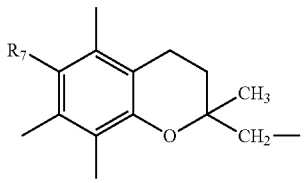

when $R_1$ is ethyl and $R_2$ is H, $R_3$ is

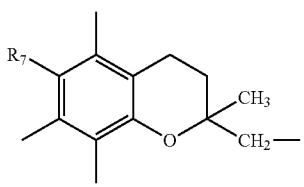

when $R_1$ is methyl and $R_2$ is OH, $R_3$ is

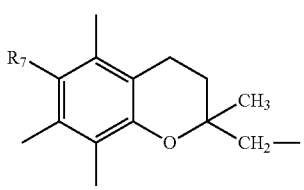

$R_2$ is selected from the group comprising hydrogen, halo, amino, methoxy, ethoxy, nitro, phenyl, di-alkyl, di-halo, trifluoromethyl, hydroxyl group, when $R_1$ is selected from the group comprising —$(CH_2)_m$—CH=CH-Φ, and

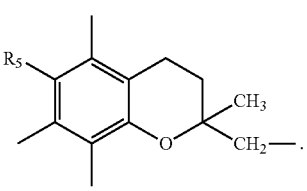

According to another definition of the invention, novel compounds of formula (I) are proposed

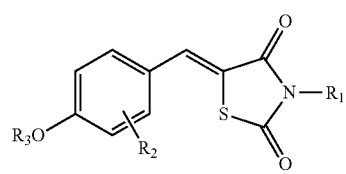

(I)

having, at a concentration of 100 μm, a hepatocyte viability preferably greater than 60%, preferably greater than 80%, and more preferentially greater than 85%, and such that:

when $R_1$ is H, then
$R_3$ is a group

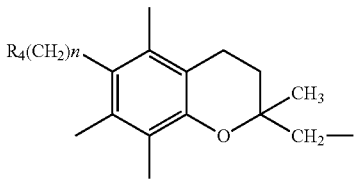

where n is greater than 1 and $R_4$ is selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, and $R_2$ is selected from the group comprising hydrogen, halo, amino, methoxy, ethoxy, nitro, phenyl, dialkyl, dihalo, trifluoromethyl, hydroxyl group;

when R1 is an alkyl group, then
$R_3$ is the group

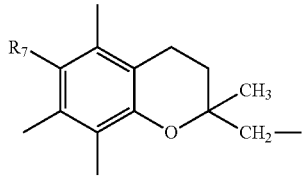

where $R_7$ is selected from the group comprising H, OH, COOH, COOR, OCOOR, $(CH_2)_q R_8$, $O(CH_2)_q R_8$, $OCO(CH_2)_q R_8$, where q is greater than or equal to 1, preferably greater than or equal to 2, $R_8$ being selected from the group comprising the groups H, OH, COOR, NRR', NHCOOR", NHM, R and R' being selected from H, an alkyl group and a benzyl group, R" being a group selected from an alkyl group and a benzyl group, and M being a fluorescent group, and $R_2$ is selected from the group comprising hydrogen, halo, amino, methoxy, ethoxy, nitro, phenyl, di-alky, di-halo, trifluoromethyl, hydroxyl;

when $R_1$ is selected from the group comprising benzyl, —$(CH_2)_m$—CH=CH-Φ,

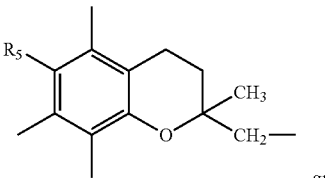

group where m is greater than or equal to 1, $R_5$ is selected from the group comprising H, OH, COOH, COOR, OCOOR, $(CH_2)_p R_9$, $O(CH_2)_p R_9$, $OCO(CH_2)_p R_9$, where p is greater than or equal to 1, preferably greater than or equal to 2, $R_9$ being selected from the group comprising the H, OH, COOR, NRR', NHCOOR", NHM group, R and R' being selected from H, an alkyl group and a benzyl group, R" being a group selected from an alkyl group and a benzyl group, and M being a fluorescent group, then $R_3$ is a group selected from the group comprising H,

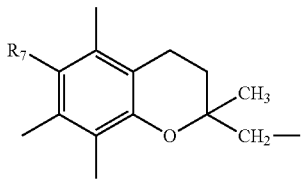

where $R_7$ is selected from the group comprising H, OH, COOH, COOR, OCOOR, $(CH_2)_q R_8$, $O(CH_2)_q R_8$, $OCO(CH_2)_q R_8$, where q is greater than or equal to 1, preferably greater than or equal to 2, $R_8$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group;

$R_2$ is selected from the group comprising hydrogen, amino, methoxy, ethoxy, nitro, phenyl, di-alkyl, hydroxyl group when $R_1$ is benzyl $R_2$ is selected from the group comprising hydrogen, halo, amino, methoxy, ethoxy, nitro, phenyl, di-alkyl, di-halo, trifluoromethyl, hydroxyl group, when $R_1$ is selected from the group comprising $—(CH_2)_m—CH=CH-\Phi$, and

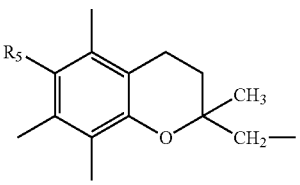

More particularly, the present invention relates to novel compounds of formula (I)

(I)

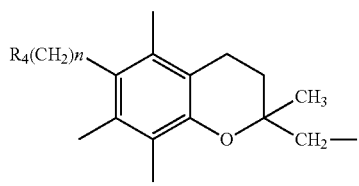

wherein:
when $R_3$ is a group

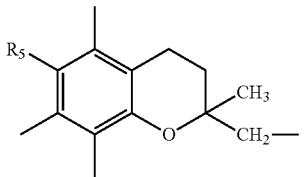

or

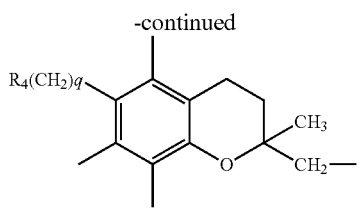

where n, q are greater than 1 and $R_4$, $R_8$ are respectively selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, then $R_1$ is selected from the group comprising H, alkyl, benzyl, $—(CH_2)_m—CH=CH-\Phi$,

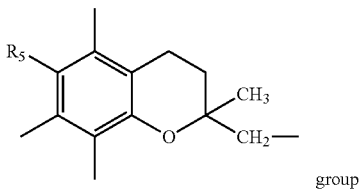

group where m is greater than or equal to 1, $R_5$ is selected from H, OH, COOH, COOR, OCOOR, $(CH_2)_p R_9$, $O(CH_2)_p R_9$, $OCO(CH_2)_p R_9$, where p is greater than or equal to 1, preferably greater than or equal to 2, $R_9$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group, $R_2$ is selected from the group comprising hydrogen, amino, methoxy, ethoxy, nitro, phenyl, di-alkyl, hydroxyl group, when $R_1$ is selected from the alkyl or benzyl group, $R_2$ is selected from the group comprising hydrogen, halo, amino, methoxy, ethoxy, nitro, phenyl, di-alkyl, di-halo, trifluoromethyl, hydroxyl groups, when $R_1$ is selected from the group comprising hydrogen, $—(CH_2)_m—CH=CH-\Phi$, and

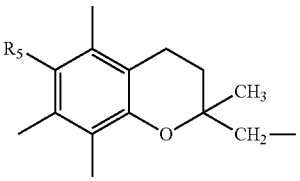

when $R_3$ is hydrogen,
$R_1$ is selected from the group comprising benzyl, $—(CH_2)m-CH=CH-\Phi$,

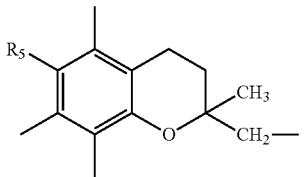

group where $R_5$ is selected from the group comprising H, OH, COOH, COOR, OCOOR, $(CH_2)_p R_9$, $O(CH_2)_p R_9$, $OCO(CH_2)_p R_9$, where p is greater than or equal to 1, preferably greater than or equal to 2, $R_9$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group;

$R_2$ is selected from the group comprising hydrogen, amino, methoxy, ethoxy, nitro, phenyl, di-alkyl, hydroxyl group when $R_1$ is benzyl $R_2$ is selected from the group comprising hydrogen, halo, amino, methoxy, ethoxy, nitro, phenyl, di-alkyl, di-halo, trifluoromethyl, hydroxyl group when $R_1$ is selected from the group comprising —$(CH_2)_m$—CH=CH-Φ, and

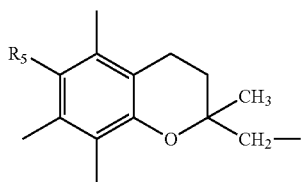

Preferably, $R_2$ is hydrogen.

Preferably n is comprised between 2 and 20 and preferentially comprised between 2 and 10 and more preferentially between 5 and 8.

When $R_4$, $R_9$ or $R_8$ are NRR' groups, $R_4$, $R_9$ or $R_8$ may be an $NH_2$ group, and NHR group (R for example being a butyl group), or NRR' group (R and R' for example forming with the nitrogen atom a piperidine residue).

The hepatocyte viability corresponds to the percentage of surviving suspended human hepatocytes after 90 minutes of incubation with the compounds of the invention present at a concentration of 100 μm.

Advantageously, the compounds of the invention further have, at a concentration of 200 μm, a hepatocyte viability preferably greater than 50%, preferably greater than 60%, more preferentially greater than 80% and still more preferentially greater than 85%.

Preferred compounds of the invention are such that $R_1$ is H and $R_4$ is for example an NRR' group, R and R' being selected from H, an alkyl group and a benzyl group, n being comprised between 2 and 20 and preferably between 2 and 10, and preferentially between 5 and 8, n may be equal to 6.

Thus, the compound for which $R_3$ is

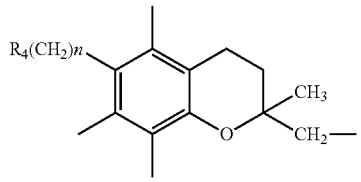

where n equals 1 and $R_1$, $R_2$ and $R_4$ are hydrogen groups, is excluded from the invention.

A particularly preferred compound is the compound of formula E:

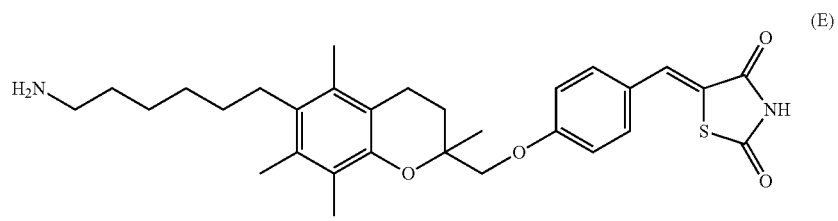 [SMILES: Cc1c(C)c2c(c(C)c1CCCCCCN)CCC(C)(COc1ccc(/C=C3\SC(=O)NC3=O)cc1)O2]

It may be present as a salt in order to increase its solubility without interfering with its activity.

A compound of the invention for which $R_4$ is an NHR group is for example:

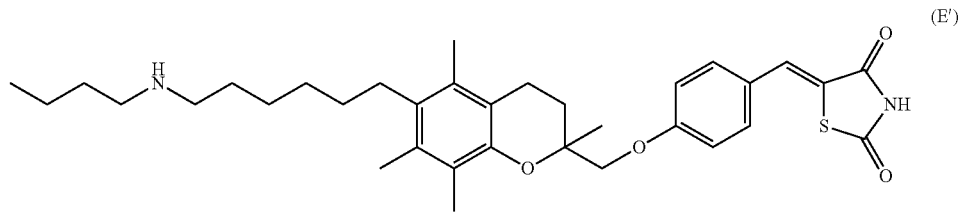 [SMILES: CCCCNCCCCCCc1c(C)c(C)c2c(c1C)CCC(C)(COc1ccc(/C=C3\SC(=O)NC3=O)cc1)O2]

A compound of the invention for which $R_4$ is an NRR' group is for example:

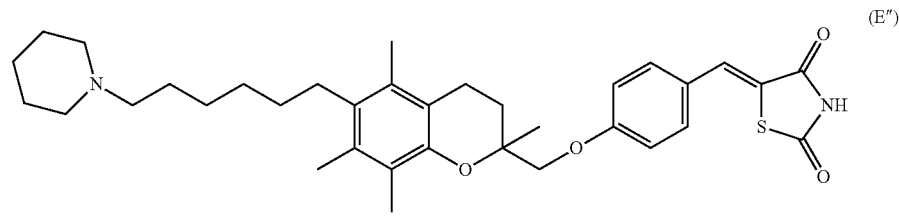 [SMILES: Cc1c(C)c2c(c(C)c1CCCCCCN1CCCCC1)CCC(C)(COc1ccc(/C=C3\SC(=O)NC3=O)cc1)O2]

Such compounds for which $R_4$ is NHR are obtained by condensing the compounds for which $R_4$ is $NH_2$ with various aldehydes, by reducing the obtained imine, for example with sodium borohydride.

Also, compounds for which $R_4$ is NRR' may be obtained by reacting the brominated synthesis intermediate (molecule No. 4 of the reaction scheme 1) with secondary amines of the morpholine, piperidine, pyrrolidine type.

Other compounds according to the invention are such that $R_1$ is H and $R_4$ is a NHCOR" group, R" being an alkyl group such as a methyl, ethyl, propyl, isopropyl, butyl, isobutyl, t-butyl or benzyl group.

A particularly preferred compound is the compound of formula C:

Such a compound is obtained by condensation of the compound E with fluorescent rhodamine isothiocyanate, at the primary amine of E.

Other compounds according to the invention are such that $R_1$ is selected from the group comprising alkyl, benzyl, $-(CH_2)_m-CH=CH-\Phi$,

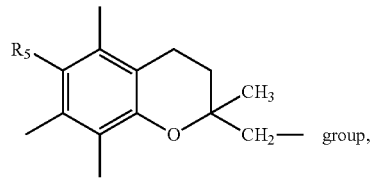

group,

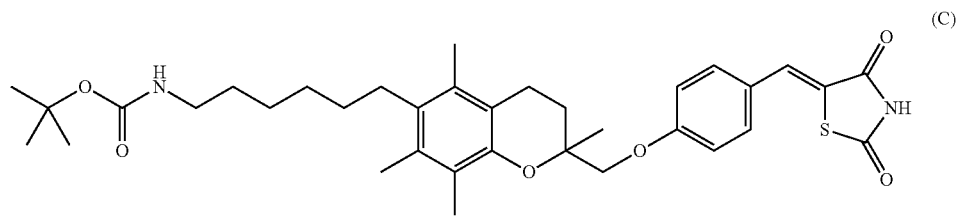 [SMILES: Cc1c(C)c2c(c(C)c1CCCCCCNC(=O)OC(C)(C)C)CCC(C)(COc1ccc(/C=C3\SC(=O)NC3=O)cc1)O2]

(C)

Other compounds according to the invention are such that $R_4$ is an NHM group, M being a fluorescent group. Preferably, M is a fluorescent group derived from a fluorophore compound selected from the group comprising fluorescein, Oregon green, rhodamine, Texas red, bodipy cyanin.

A particularly preferred compound is the compound Q, for which $R_1$ is H and M is derived from rhodamine, of formula:

where m is greater than or equal to 1, $R_5$ is selected from the group comprising H, OH, COOH, COOR, OCOOR, $(CH_2)_p R_9$, $O(CH_2)_p R_9$, $OCO(CH_2)_p R_9$, where p is greater than or equal to 1, preferably greater than or equal to 2, $R_9$ being selected from the group comprising H, OH, COOR, NRR', NHCOOR", NHM, R and R' being selected from H, an alkyl group and a benzyl group, R" being a group selected from

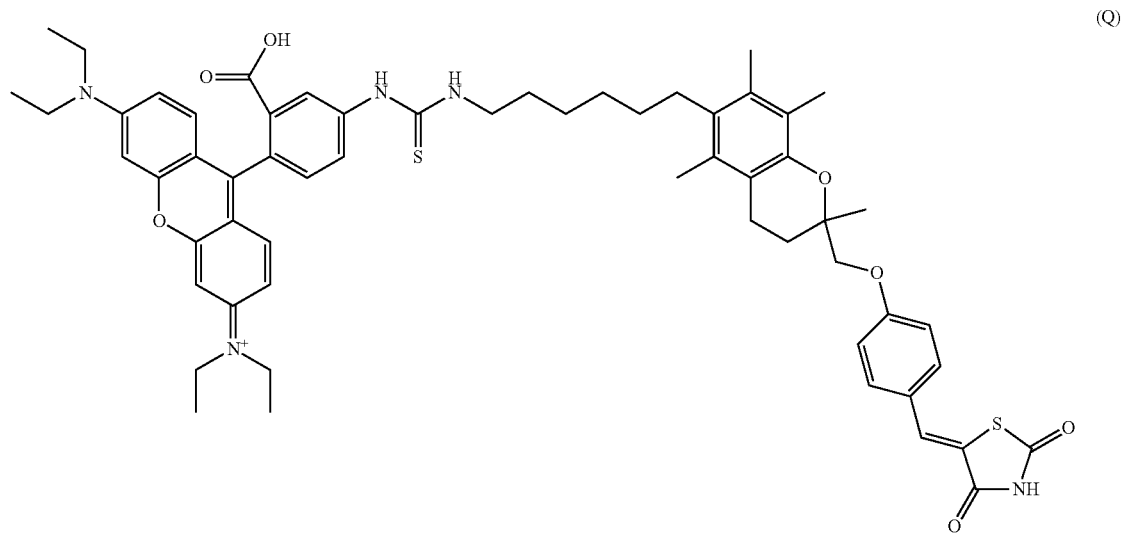 [SMILES: CCN(CC)c1ccc2c(-c3ccc(NC(=S)NCCCCCCc4c(C)c(C)c5c(c4C)CCC(C)(COc4ccc(/C=C6\SC(=O)NC6=O)cc4)O5)cc3C(=O)O)c3ccc(=[N+](CC)CC)cc-3oc2c1]

(Q)

an alkyl group and a benzyl group, and M being a fluorescent group and R$_3$ is the group

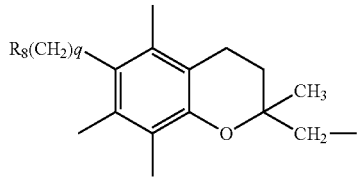

where q is greater than or equal to 1, preferably greater than or equal to 2, R$_8$ being selected from the group comprising H, OH, COOR, NRR', NHCOOR", NHM group, R and R' being selected from H, an alkyl group and a benzyl group, R" being a group selected from an alkyl group and a benzyl group, and M being a fluorescent group.

Among these compounds, preferred compounds according to the invention are such that R$_1$ is an alkyl group, preferably a methyl or ethyl group.

Among these compounds, preferred compounds according to the invention are such that R$_1$ is an alkyl group, for example a methyl group, and R$_3$ is the group

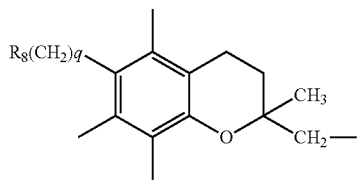

R$_8$ and q being defined above.

Among these compounds, preferred compounds are such that R$_1$ is an alkyl group, for example a methyl, and R$_8$ is an NRR' group, R and R' being selected from H, an alkyl group and a benzyl group, q being comprised between 1 and 20 and preferably between 1 and 10, and preferentially between 5 and 8, q may be equal to 6.

A particularly preferred compound is the compound of formula D:

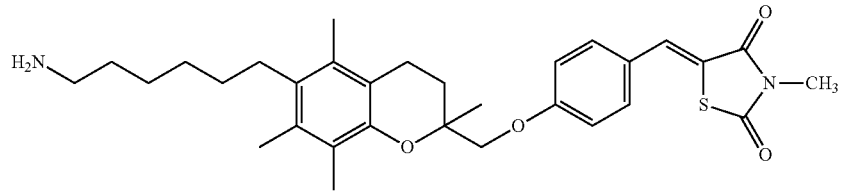

It may be present as a salt.

Other compounds according to the invention are such that R$_1$ is selected from the group comprising alkyl, benzyl, —(CH$_2$)$_m$—CH═CH-Φ,

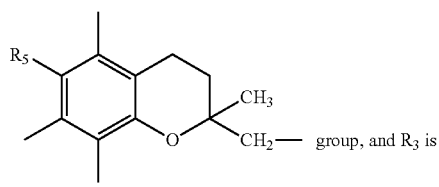

-continued

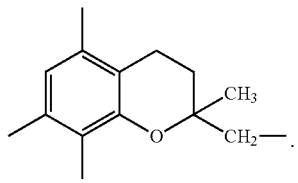

Among these compounds, preferred compounds according to the invention are such that R$_1$ is an alkyl group, preferably a methyl or ethyl.

Among these compounds, preferred compounds according to the invention are such that R$_1$ is a methyl group.

A particularly preferred compound is the compound of formula P:

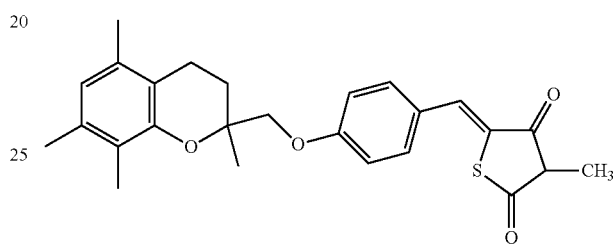

Other compounds according to the invention are such that R$_1$ is selected from the group comprising alkyl, benzyl, —(CH$_2$)$_m$—CH═CH-Φ,

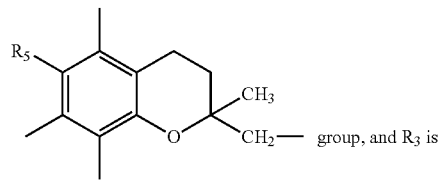

-continued

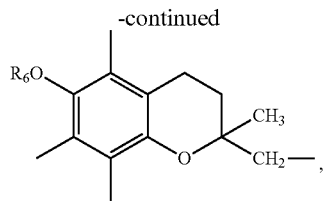

where R$_6$ is selected from the group comprising H, COOR, R being an alkyl group, (CH$_2$)$_q$R$_8$, CO(CH$_2$)$_q$R$_8$, where q is greater than or equal to 1, q being preferably comprised between 1 and 20 and preferably between 1 and 10 and preferentially between 5 and 8, q may be equal to 7.

Preferably, R$_1$ is an alkyl group, preferably a methyl.

Preferably, $R_1$ is an alkyl group, preferably a methyl and $R_3$ is

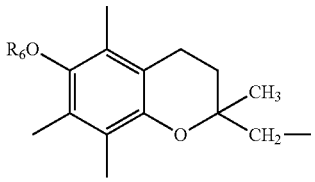

where $R_6$ is selected from the group comprising H, COOR, $(CH_2)_qR_8$, $CO(CH_2)_qR_8$, where R is alkyl and q is greater than or equal to 1.

Preferably, R is an alkyl group such as a methyl, ethyl, propyl, isopropyl, butyl, isobutyl, t-butyl group.

Among these compounds, the preferred compounds are defined by $R_1$ and $R_6$ such that:

| $R_1$ | $R_6$ |
|---|---|
| $CH_3$ | COOtBu (compound F) |
| $CH_3$ | H (compound J) |
| $CH_3$ | $CO(CH_2)_qNH_2$ |

A particularly preferred compound is the compound of formula J defined below.

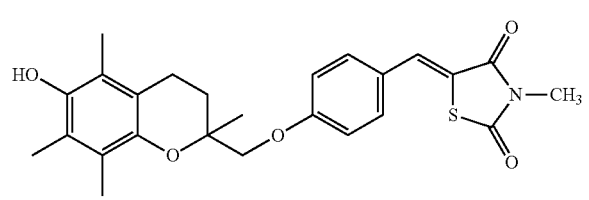

(J)

A particularly preferred compound is the compound of formula B:

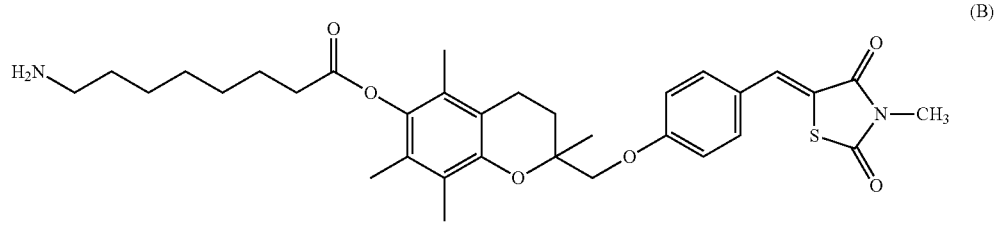 [SMILES: Cc1c(C)c2c(c(C)c1OC(=O)CCCCCCCN)CCC(C)(COc1ccc(/C=C3\SC(=O)N(C)C3=O)cc1)O2]

(B)

It may be present as a salt.

Other compounds of the invention are such that $R_1$ is a benzyl group and $R_3$ is

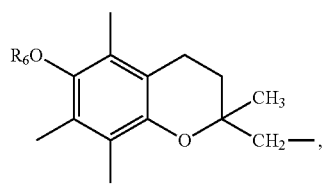

$R_6$ being selected from the group comprising H, COOR, $(CH_2)_qR_8$, $CO(CH_2)_qR_8$ where q is greater than or equal to 1, q being preferably comprised between 1 and 20, and more preferentially between 1 and 10 and preferentially between 5 and 8.

Preferably R is an alkyl group such as a methyl, ethyl, propyl, isopropyl, butyl, isobutyl and t-butyl group.

Among these compounds, a preferred compound is such that $R_1$ is a benzyl group and $R_6$ is H.

Thus, a preferred compound is the compound of formula G:

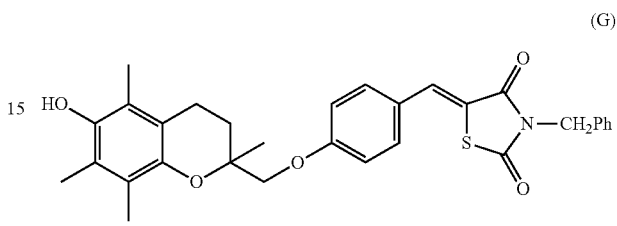

(G)

Other compounds of the invention are defined by $R_3$ and $R_1$ such that:

| $R_3$ | $R_1$ |
|---|---|
| H | $-(CH_2)_m-CH=CH-\Phi$ |
| H | 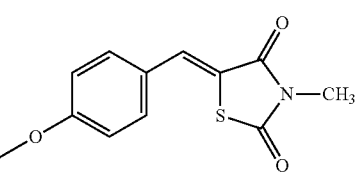 | m is preferably comprised between 1 and 5 and preferentially between 1 and 3.

$R_5$ is preferably OH or OCOOR R being an alkyl group such as a methyl, ethyl, propyl, isopropyl, butyl, isobutyl, t-butyl group.

Among these compounds, a preferred compound is the compound of formula A:

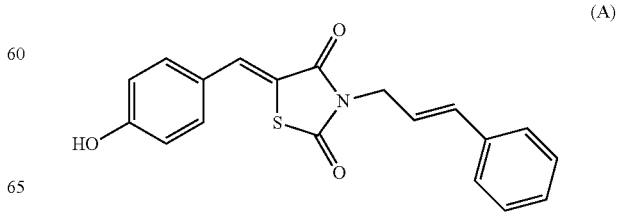

(A)

Another preferred compound is the compound of formula H:

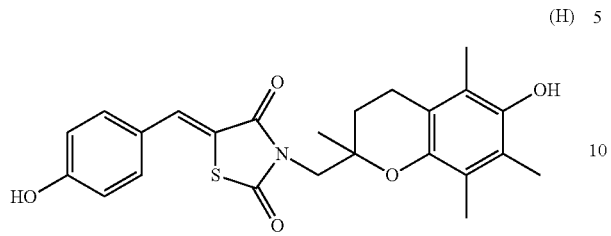

Of course it is understood that all the optical and geometrical isomers, notably enantiomers, diastereoisomers and mixtures thereof, notably racemic mixtures, as well as addition salts with mineral or organic acids or with mineral or organic bases of the compound described above belong to the present invention.

The compounds according to the invention are non-toxic on primary cultures of human hepatocytes, unlike TGZ or known derivatives. Further they have an anti-proliferative activity on lines of human cancer cells much greater than TGZ and greater than that of known derivatives.

More particularly, the compounds for which $R_3$ is

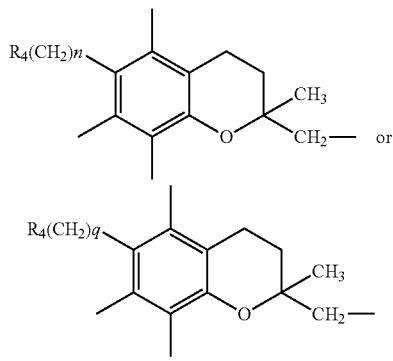

not having any oxygen bound to the chromane group in position 6 and having instead an alkyl chain, surprisingly and unexpectedly appear as compounds having low hepatic toxicity while retaining anti-proliferative activity.

On the other hand, it also appeared surprisingly and unexpectedly that the compounds for which the nitrogen of the thiazolidinedione is substituted with a group as defined above, have low hepatic toxicity while retaining anti-proliferative activity.

The present invention also relates to a method for synthesizing compounds of formula (1) wherein $R_3$ is the group

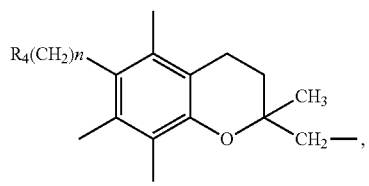

said method comprising the preparation of an intermediate molecule of formula (II)

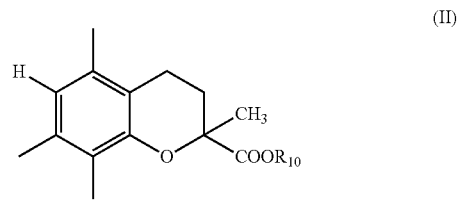

wherein $R_{10}$ is an alkyl group.

The present invention also relates to an intermediate molecule of formula (II)

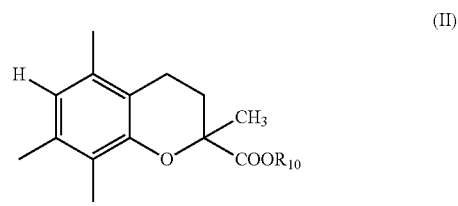

where $R_{10}$ is an alkyl group such as a methyl, ethyl, for preparing compounds of formula (1) as defined above wherein $R_3$ is

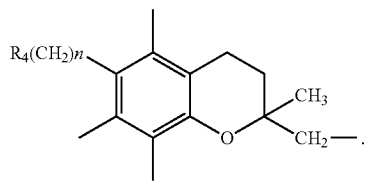

The present invention also relates to a method for synthesizing the intermediate molecule of formula (II) as defined above comprising:
  a step for esterification of the compound of formula (III) with an alcohol $R_{10}OH$

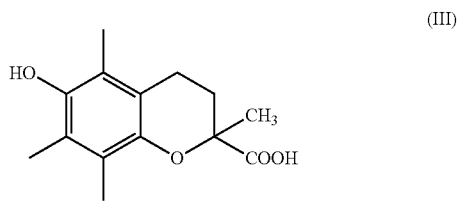 [SMILES: Cc1c(C)c2c(c(C)c1O)CCC(C)(C(=O)O)O2]

a step for functionalizing the function OH of the compound III esterified with a leaving group,
  a step for hydrogenation under pressure in the presence of an organic base, with which the intermediate molecule of formula (II) may be obtained.

The last two steps are based on a procedure described in the literature ((E. Mandavian, S. Sangsura, G. Landry, J. Eytina, B. A. Salvatore, Tetrahedron Lett. 50 (2009) 19-21).

Preferably, the leaving group used during the functionalization step of the OH function is for example $OSO_2CF_3$, $OSO_2PhCH_3$ or $OSO_2CH_3$, the step taking place in the presence of Tf$_2$O (triflic anhydride) or TOSCl (tosyl chloride) or MESCl (mesyl chloride) and pyridine.

The organic base used during the hydrogenation step is for example triethylamine.

Another method for synthesizing the intermediate molecule of formula (II) defined above in a single step may be proposed:

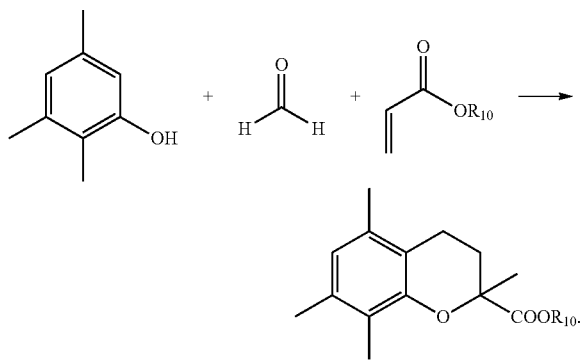

The reagents are available commercially.

This method is based on a procedure described by E. A. Couladouros et al. Journal of Organic Chemistry 2007, 72, 6735-6741.

The present invention also relates to a pharmaceutical composition, containing as an active ingredient, an effective dose of a compound of formula (I) as defined above, or of one of its addition salts with pharmaceutically acceptable mineral and organic acids or mineral or organic bases.

The active ingredient may be mixed with at least one pharmaceutically acceptable excipient and/or with at least one other active ingredient.

These excipients are known to one skilled in the art and will be adapted to the pharmaceutical form and to the desired method of administration. The pharmaceutical compositions according to the invention appear in all the forms known to one skilled in the art, notably suitable for administration via an oral, sublingual, intramuscular, intravenous, topical, local, intranasal, transdermal or rectal route. The pharmaceutical compositions may thus appear as gelatin capsules, tablets, granules, suppositories, injectable preparations, creams, prepared according to the usual methods.

The present invention also relates to a pharmaceutical compound or composition as defined above, for use as a drug.

The present invention also relates to a pharmaceutical compound or composition as defined above, for use as a drug for preventing or treating cancer, and more particularly breast cancer.

The following examples illustrate the present invention without however limiting the scope thereof.

Preparations

General Comments:

The solvents and the liquid reagents were purified and dried according to recommended procedures. The water used for washing the organic solutions is distilled water. The thin layer chromatography analyses were achieved according to the standard procedures on Kieselgel 60 F254 (Merck) plates. The compounds were used by using a UV lamp (254 nm) and a solution of cerium sulfate tetrahydrate and of phosphomolybdic acid in 10% aqueous sulfuric acid as a developer. An ethanol solution of ninhydrin (0.3%) and of acetic acid (3%) is also sometimes used. The chromatography columns were made with silica, silica gel SI60 (63-200 µm) (Merck). Certain chromatographies (if indicated) were carried out with silica, silica gel 60H (5-40 µm) (Merck) with an <<Axial® Modul Prep>> machine, operating at 8 bars with a column with a diameter of 20 mm. The $^1$H NMR spectra were recorded on a Bruker DPX250 (250 MHz) spectrometer. The chemical shifts (δ) are given in ppm relatively to the residual peak of the solvent. The mass spectra were obtained on a VG-Platform Micromass-Waters (ESI+/−) spectrometer.

The elementary analyses were carried out on a Thermofinnagan Flash EA1112 apparatus.

Synthesis of the compounds of formulae C, D and E:

The synthesis of these derivatives is carried out according to the following

Scheme 1. Synthesis of the compounds C, D and E.

Reaction Scheme 1:

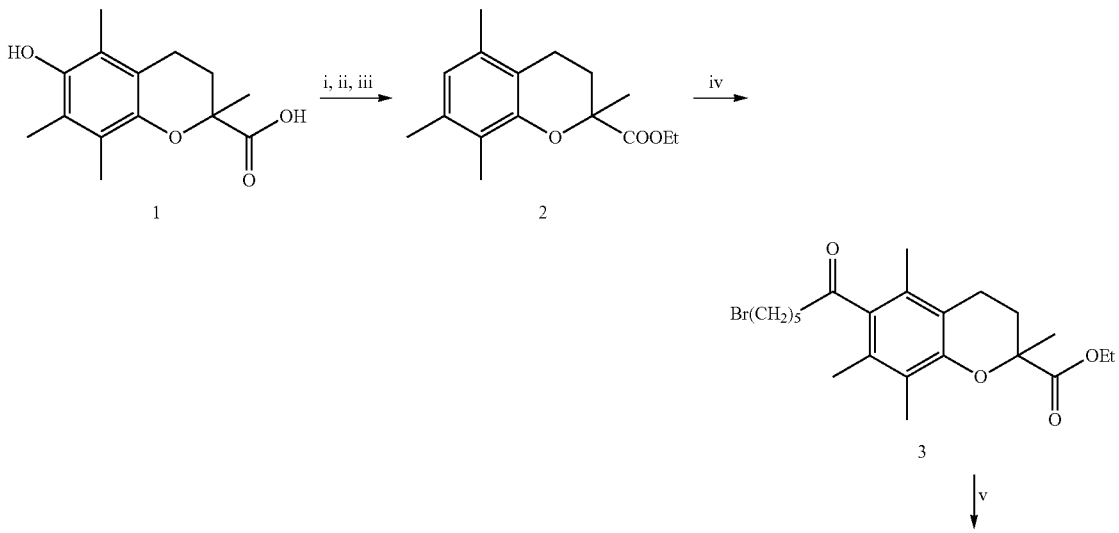

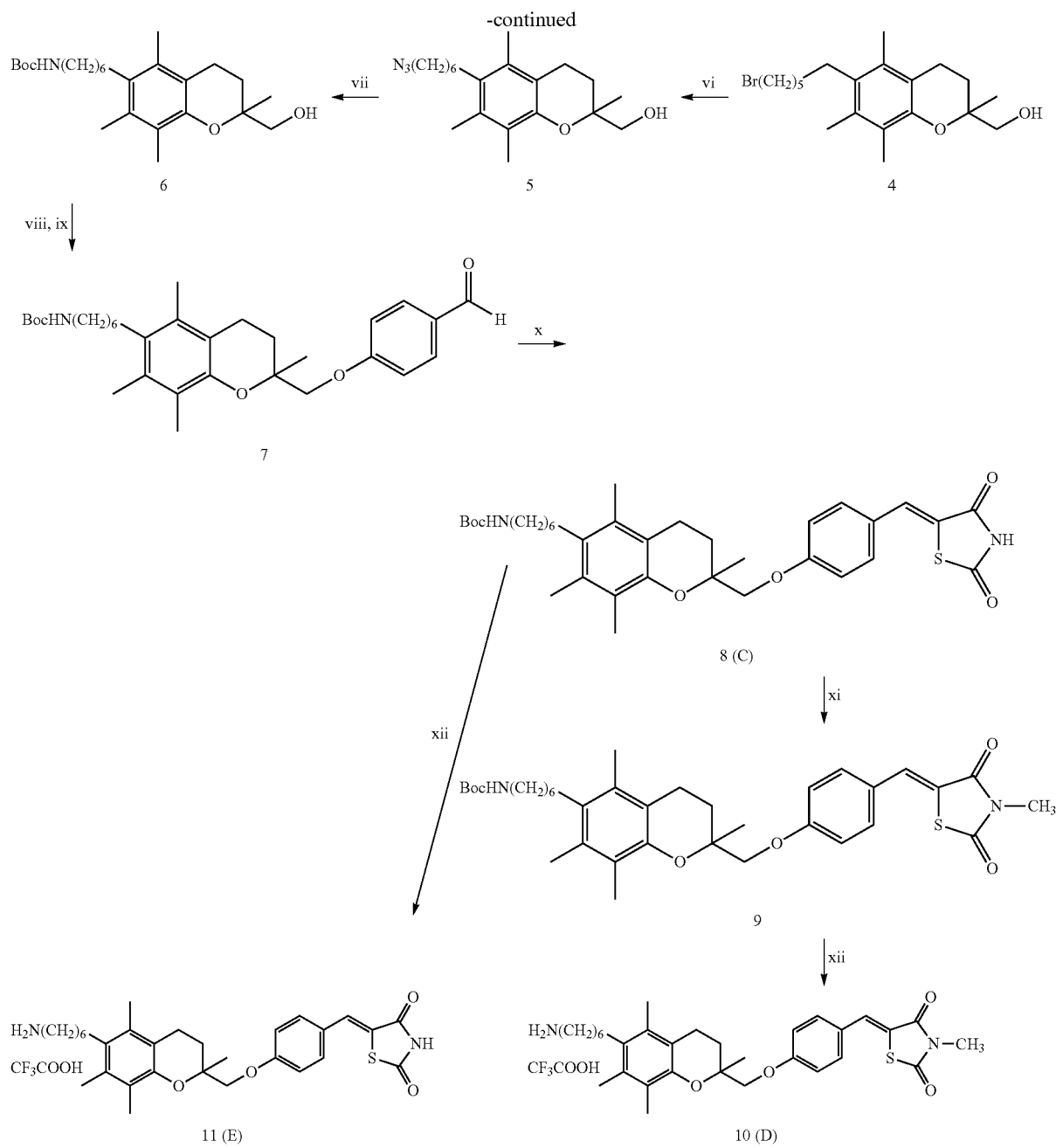

Reagents and conditions: i EtOH, cat. p-TSA, reflux 95%, ii Tf₂O, pyr., 99%: iii TEA, H₂ 70 psi (487 kPa), 10% Pd/C 96%: iv Br(CH₂)₅COCl, AlCl₃ 70%; v LiAlH₄, AlCl₃ 98%, vi NaN₃ 98%; vii H₂ 1 atm, Pd/C, Boc₂O 70%, viii Tf₂O, Pyr. quant. Pyr.; ix 4-hydroxybenzaldehyde, K₂CO₃ 67%; x 2,4-thiazolidinedione, piperidine, benzoic acid, 80%; xi CH₃I, K₂CO₃ 65%; xii trifluoroacetic acid 54% (10, compound D), 53% (11, compound E).

(±) Tert-butyl(6-{2-[4-(2,4-dioxo-thiazolidin-5-ylidenemethyl)-phenoxymethyl]-2,5,7,8-tetramethyl-chroman-6-yl}-hexyl)-carbamate (compound C)

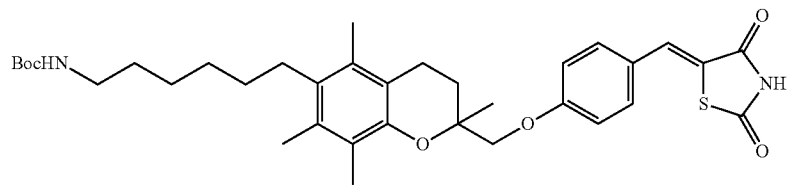 [SMILES: Cc1c(C)c2c(c(C)c1CCCCCCNC(=O)OC(C)(C)C)CCC(C)(COc1ccc(/C=C3\SC(=O)NC3=O)cc1)O2]

Step i: To a solution of (±) 6-hydroxy-2,5,7,8-tetramethylchroman-2-carboxylic acid (Trolox®) 1 (4.46 g; 18.82 mmol) in EtOH (175 ml), is added p-toluene sulfonic acid (361 mg; 1.90 mmol), and the mixture is heated with reflux for 96 hours. The solution is concentrated in vacuo, and the residue is dissolved in AcOEt (150 ml). The resulting solution is washed with an aqueous solution of 5% $NaHCO_3$ (2×50 ml) and a saturated NaCl solution (2×50 ml). The organic phase is dried ($MgSO_4$) and the solvent is evaporated. The product is carefully dried so as to obtain 4.98 g of ethyl ester in the form of white crystals (17.90 mmol yield 95%).

Step ii: to a solution of 500 mg (1.80 mmol) of the previous ester in dry $CH_2Cl_2$ (10 mL) under argon, is added pyridine (872 µL, 10.78 mmol) and the solution is cooled to 0° C. Next, triflic anhydride (453 µL, 2.69 mmol) is added dropwise and the solution is stirred for 1 h at room temperature. The solution is diluted with $CH_2Cl_2$ (20 mL) and washed with water (2×30 mL), dried ($MgSO_4$) and dry concentrated. The liquid residue is purified by chromatography on a silica column (hexane/AcOEt, 85:15) in order to obtain 735 mg (1.79 mmol; yield 99%) of triflate as a colorless liquid.

Step iii: 10% palladium on coal (3.00 g) are first introduced into the container of a Parr hydrogenator, in order to avoid any inflammation of the solvent. The palladium/coal used is obtained from Fisher/ACROS (Catalogue No: 19503-0500). A solution of the previous triflate (4.96 g; 12.09 mmol) in THF (40 ml) is added to the container, followed by MeOH (80 ml) and TEA (7.4 ml; 53.22 mmol). The suspension is stirred under pressure of 70 psi of hydrogen for 20 hours at room temperature, and then filtered on Celite® and the resulting solution is concentrated in vacuo. Silica column chromatography (hexane/AcOET, 90:10) gives 3.03 g (11.55 mmol; yield 96%) of compound 2 ((±) ethyl 2,5,7,8-tetramethyl-chroman-2-carboxylate) as a colorless liquid which during its storage at 4° C. gives white crystals with a low melting point (about 30° C.). $^1$H NMR ($CDCl_3$) δ: 1.19 (t, J=7.1 Hz, 3H, $COOCH_2CH_3$); 1.62 (s, 3H, $CH_3$); 1.82-1.95 (m, 1H, chromane 3-HaHb); 2.13 (s, 3H, $ArCH_3$); 2.16 (s, 3H, $ArCH_3$); 2.21 (s, 3H, $ArCH_3$); 2.38-2.69 (m, 3H, chromane 3-HaHb and 4-$H_2$); 4.14 (q, J=7.1 Hz, 2H, $COOCH_2CH_3$); 6.58 (s, 1H, $H_{arom}$). ESI-MS (positive mode): m/z=285.21 $[M+Na]^+$. Anal. Calc, for $C_{16}H_{22}O_3$ (262.4): C, 73.25; H, 8.45. Found: C, 73.63; H, 8.20.

Step iv: preparation of the intermediate acid chloride: a solution of 1-bromohexanoic acid (2.02 g; 10.3 mmol) and of thionyl chloride (2.2 ml; 30.8 mmol) in dry $CH_2Cl_2$ (10 ml) is refluxed under argon for 4 hours. The solvent is removed in vacuo several hours in order to remove any excess of thionyl chloride. The obtained colorless oil is directly used in the following step without any additional purification. Friedel-Craft reaction: a suspension of the previous acid chloride and of $AlCl_3$ (1.44 g; 10.8 mmol) at 0° C. in dry $CH_2Cl_2$ (3 mL) is gently added to a solution of the compound 2 in dry $CH_2Cl_2$ (4 mL). The reaction is stirred under argon at 0° C. for 1 hour and then at room temperature overnight. The reactor is regularly purged with argon for removing HCl. The reaction is carefully stopped with cold distilled water (6 mL) and an aqueous solution of hydrochloric acid (2 mL). The organic phase is separated and washed with an aqueous solution of 5% $NaHCO_3$ (10 mL), dried with $MgSO_4$, filtered and the solvent is removed in vacuo in order to obtain a yellow liquid subsequently purified by silica column chromatography (hexane:AcOEt 95:5) in order to obtain the compound 3 ((±) ethyl 6-(6-bromo-hexanoyl)-2,5,7,8-tetramethyl-chroman-2-carboxylate) in the form of a colorless liquid (690 mg; 1.57 mmol, yield 70%).

Step v: to a suspension of $LiAlH_4$ (176 mg; 4.64 mmol) in dry $Et_2O$ (6 ml) under argon is slowly added a solution of $AlCl_3$ (413 mg; 3.10 mmol). Five minutes later, a solution of compound 3 (680 mg; 1.55 mmol) and $AlCl_3$ (206 mg; 1.55 mmol) in dry $Et_2O$ (12 ml) is added. The mixture is stirred under argon at room temperature for 2 hours and are then added carefully cold water (24 ml) and an aqueous 6M solution of $H_2SO_4$. The organic phase is separated and the aqueous phase is extracted with AcOEt (2×1 5 mL). The organic phases are collected and then washed with an aqueous solution of $Na_2CO_3$ 2M (10 mL), dried ($MgSO_4$), filtered and the solvent is evaporated in vacuo in order to obtain the compound 4 ((±) [6-(6-bromo-hexyl)-2,5,7,8-tetramethyl-chroman-2-yl]-methanol) in the form of a colorless liquid (592 mg; 1.54 mmol; yield 98%) which is directly used for the following step without any additional purification.

Step vi: a suspension of compound 4 (592 mg; 1.54 mmol) and of $NaN_3$ (1.00 g; 15.4 mmol) in dry DMF (15 mL) is heated to 80° C. for 6 hours. The mixture is cooled to room temperature, diluted with AcOEt (60 mL) and washed with a saturated NaCl solution (2×50 ml) and with water (50 mL), dried ($MgSO_4$), filtered and the solvent is evaporated in vacuo in order to obtain the compound 5 ([6-(6-azido-hexyl)-2,5,7,8-tetramethyl-chroman-2-yl]-methanol) in the form of a colorless liquid (532 mg; 1.54 mmol; yield 98%), which is directly used for the following step without any additional purification.

Step vii: a suspension of compound 5 (532 mg; 1.54 mmol), Pd/C (53 mg) and $Boc_2O$ (403 mg; 1.85 mmol) in dry MeOH (10 mL) is stirred at room temperature under a hydrogen atmosphere for 12 hours. The mixture is filtered on Celite® and MeOH is evaporated in vacuo. The residue is dissolved in AcOEt (20 mL) and the solution is washed with an aqueous solution of a 5% citric acid (2×15 mL), an aqueous solution of 5% $NaHCO_3$ (2×1 5 mL) and of water (20 mL), dried ($MgSO_4$), filtered and the solvent is evaporated in vacuo in order to obtain a pale yellow liquid which is purified by silica column chromatography (hexane:EtOAc 8:2) in order to obtain the compound t ((±) tert-butyl[6-(2-hydroxymethyl-2,5,7,8-tetramethyl-chroman-6-yl)-hexyl]-carbamate) in the form of a colorless oil (452 mg; 1.08 mmol, yield 70%).

Step viii: a solution of anhydrous pyridine (430 µL; 5.39 mmol) in dry $CH_2Cl_2$ (5 mL) is cooled to 0° C., and is then added trifluoromethanesulfonic anhydride (210 µL; 1.26 mmol) under argon, dropwise. A solution of compound 6 (377 mg; 0.90 mmol) in dry $CH_2Cl_2$ (5 mL) is added to the mixture. The solution is stirred at 0° C. for 20 mins and the solvent is evaporated. The pyridine excess is co-evaporated twice with toluene and the residue is dissolved in AcOEt (25 mL). The organic phase is washed with an aqueous solution of 5% $NaHCO_3$ (2×15 mL) and a saturated solution of NaCl (20 mL), dried (MgSO4), filtered and the solvent is evaporated for obtaining the desired triflate as a brown liquid directly used in the next step.

Step ix: to a solution of the previous triflate in dry DMF (3 mL) are added 4-hydroxybenzaldehyde (164 mg; 1.35 mmol) and $K_2CO_3$ (232 mg; 1.68 mmol). The mixture is stirred under argon at room temperature for two days, and then water (8 mL) is added. The suspension is extracted with AcOEt (2×20 mL). The organic phase is washed with an aqueous solution of 5% $NaHCO_3$ (2×15 mL) and a saturated solution of NaCl (20 mL), dried ($MgSO_4$), filtered and the solvent is evaporated in order to obtain a yellow liquid subsequently purified by silica column chromatography (hexane:AcOEt 9:1) in order to obtain the compound 7 ((±) tert-butyl {6-[2-(4-formyl-phenoxymethyl)-2,5,7,8-tetramethyl-chroman-6-yl]-hexyl}-carbamate) in the form of a white solid (316 mg; 0.60 mmol; yield 67%).

Step x: a solution of compound 7 (68 mg; 0.13 mmol), 2,4-thiazolidinedione (31 mg; 0.26 mmol), piperidine (70 µL; 0.07 mmol) and benzoic acid (80 mg; 0.07 mmol) in dry toluene (3 mL) is refluxed overnight under argon. The mixture is cooled to room temperature, diluted with AcOEt (10 mL), washed with a 1N HCl solution (5 mL), a solution of 5% NaHCOs (5 mL) and a saturated solution of NaCl (5 mL), dried (MgSO$_4$), filtered and then the solvent is evaporated for obtaining a yellow liquid which is purified by precipitation in cold MeOH in order to obtain the compound of formula C (66 mg; 0.10 mmol, yield 81%) in the form of a slightly yellow solid.

$^1$H NMR (CDCl$_3$) δ: 1.43 (s, 3H, CH$_3$); 1.36-1.44 (m, 4H, linker-CH$_2$); 1.45 (s, 9H, –tBu); 1.55-1.69 (m, 4H, linker-CH$_2$); 1.82-1.98 (m, 1H, 3-HaHb chromane); 2.10-2.14 (m, 1H, 3-HaHb chromane); 2.09 (s, 3H, ArCH$_3$); 2.15 (s, 3H, ArCH$_3$); 2.19 (s, 3H, ArCH$_3$); 2.52-2.74 (m, 4H, 4-H$_2$ chromane, CH$_2$ linker); 3.06-3.18 (m, 2H, CH$_2$ linker); 3.96; 4.06 (system AB, J=9.4 Hz, 2H, CH$_2$O); 4.50 (sl, 1H, NHBoc); 7.01 (d, J=9.0 Hz, 2H, H$_{arom}$), 7.43 (d, J=9.0 Hz, 2H, H$_{arom}$), 7.80 (s, 1H, ArCH=); 8.41 (si, 1H, NH). ESI-MS (positive mode): m/z=645.29 [M+Na]+Anal. calc. for C$_{35}$H$_{46}$N$_2$O$_6$S, ⅓H$_2$O (628.8): C, 66.85; H, 7.48; N, 4.45. Found: C, 66.83; H, 7.27; N, 4.47.

trifluoroacetic acid (1 mL) is added. The reaction is brought to room temperature and stirred for 3 hours. The solvent is evaporated and the acid excess is co-evaporated with MeOH (5 times). The obtained solid is washed with Et$_2$O in order to obtain the compound of formula D (17 mg; 26.1 µmol, yield 54%) in the form of a colorless solid. $^1$H NMR (CDCl$_3$) δ: 1.42 (s, 3H, CH$_3$); 1.28-1.57 (m, 6H, CH$_2$linker); 1.57-1.80 (m, 2H, CH$_2$ linker); 1.82-1.98 (m, 1H, 3-HaHb chromane); 2.08-2.17 (m, 1H, 3-HaHb chromane); 2.08 (s, 3H, ArCH$_3$); 2.13 (s, 3H, ArCH3); 2.17 (s, 3H, ArCH$_3$); 2.75 (m, 4H, 4-H2 chromane, CH$_2$ linker); 2.80-3.10 (m, 2H, CH$_2$ linker); 3.23 (s, 3H, NCH$_3$); 3.95, 4.05 (system AB, J=9.4 Hz, 2H, CH$_2$O); 6.99 (d, J=8.0 Hz, 2H, H$_{arom}$); 7.43 (d, J=8.0 Hz, 2H, H$_{arom}$); 7.85 (s, 1 H, ArCH=); 7.85-8.02 (sl, 2H, NH$_2$). ESI-MS (positive mode): m/z=537.29 [M+H]+. Anal. calc., for C$_{33}$H$_{41}$F$_3$N$_2$O$_6$S (536.2): C, 60.91; H, 6.35; N, 4.30. Found: C, 60.44; H, 6.31; N, 4.20.

(±) 5-{4-[6-(6-amino-hexyl)-2,5,7,8-tetramethyl-chroman-2-ylmethoxy]-benzylidene}-3-methyl-thiazolidine-2,4-dione trifluoroacetate (compound D)

(±) 5-{4-[6-(6-amino-hexyl)-2,5,7,8-tetramethyl-chroman-2-ylmethoxy]-benzylidene}thiazolidine-2,4-dione trifluoroacetate (compound E)

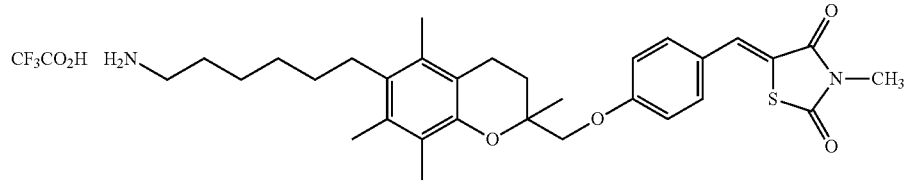 [SMILES: "CF3CO2H" ; Cc1c(C)c2c(c(C)c1CCCCCCN)CCC(C)(COc1ccc(/C=C3\SC(=O)N(C)C3=O)cc1)O2]

Step xi: to a solution of the compound C (230 mg; 0.37 mmol) in dry DMF (3 ml) are added K$_2$CO$_3$ (66 mg; 0.48 mmol) and methyl iodide (28 (µL; 0.44 mmol). The mixture is stirred under argon at 80° C. for 3 hours. It is then diluted

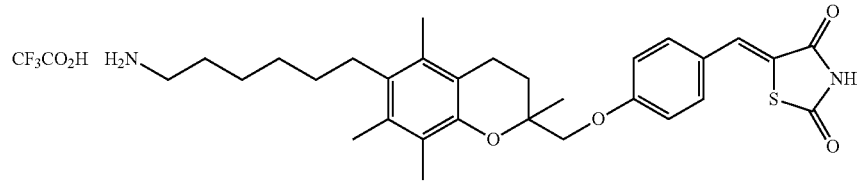 [SMILES: "CF3CO2H" ; Cc1c(C)c2c(c(C)c1CCCCCCN)CCC(C)(COc1ccc(/C=C3\SC(=O)NC3=O)cc1)O2]

with AcOEt (30 mL) and the solution is washed with a saturated NaCl solution (20 mL) and water (20 mL), dried (MgSO$_4$), filtered and the solvent is evaporated in vacuo in order to obtain a yellow liquid which is purified by precipitation in cold MeOH in order to obtain the compound 9 ((±) tert-butyl(6-{2,5,7,8-tetramethyl-2-[4-(3-methyl-2,4-dioxo-thiazolidin-5-ylidenemethyl)-phenoxymethyl]-chroman-6-yl}-hexyl)-carbamate) in the form of a colorless solid (154 mg; 0.24 mmol, yield 65%).

Step xii: a solution of the compound 9 9 (30 mg; 48.2 µmol) in dry CH$_2$Cl$_2$ (2 mL) is cooled to 0° C., and then Step xii: as previously, a solution of the compound C (44 mg; 70.6 (µmol) in dry CH$_2$Cl$_2$ (2 mL) is cooled to 0° C., and then trifluoroacetic acid (1 mL) is added. The reaction is brought to room temperature and stirred for 3 hours. The solvent is evaporated and the acid excess is co-evaporated with MeOH (5 times). The obtained yellow solid is washed with Et$_2$O in order to obtain the compound of formula E (24 mg; 37.7 µmol; yield 53%) in the form of a pale yellow solid. 1H NMR (MeOD) δ: 1.43 (s, 3H, CH$_3$); 1.57 (m, 6H, CH2 linker); 1.60-1.79 (m, 2H, CH$_2$ linker); 1.85-2.00 (m, 1H, 3-HaHb chromane); 1.90 (s, 3H, ArCH$_3$); 2.06-2.18 (m, 1H, 3-HaHb chromane; 2.18 (s, 3H, ArCH$_3$); 2.19 (s, 3H, ArCH$_3$); 2.59-2.76 (m, 4H, 4-H2 chromane, CH$_2$ linker); 2.95 (t, J=7.3 Hz, 2H, CH2 linker); 4.09 (s, 2H, CH2O); 7.08

(d, J=8.8 Hz, 2H, H$_{arom}$); 7.50 (d, J=8.8 Hz, 2H, H$_{arom}$); 7.76 (s, 1H, ArCH=). ESI-MS (positive mode): m/z=523.26 [M+H]$^+$. Anal. calc., for C$_{32}$H$_{39}$F$_3$N$_2$O$_6$S, H$_2$O (654.74): C, 58.70; H, 6.31; N, 4.28. Found: C, 59.08; H, 6.18; N, 4.18.

Synthesis of the Compounds of Formula G, F and J

Their synthesis is carried out according to the following Reaction Scheme 2:

Scheme 2: Synthesis of compounds G, F and J.

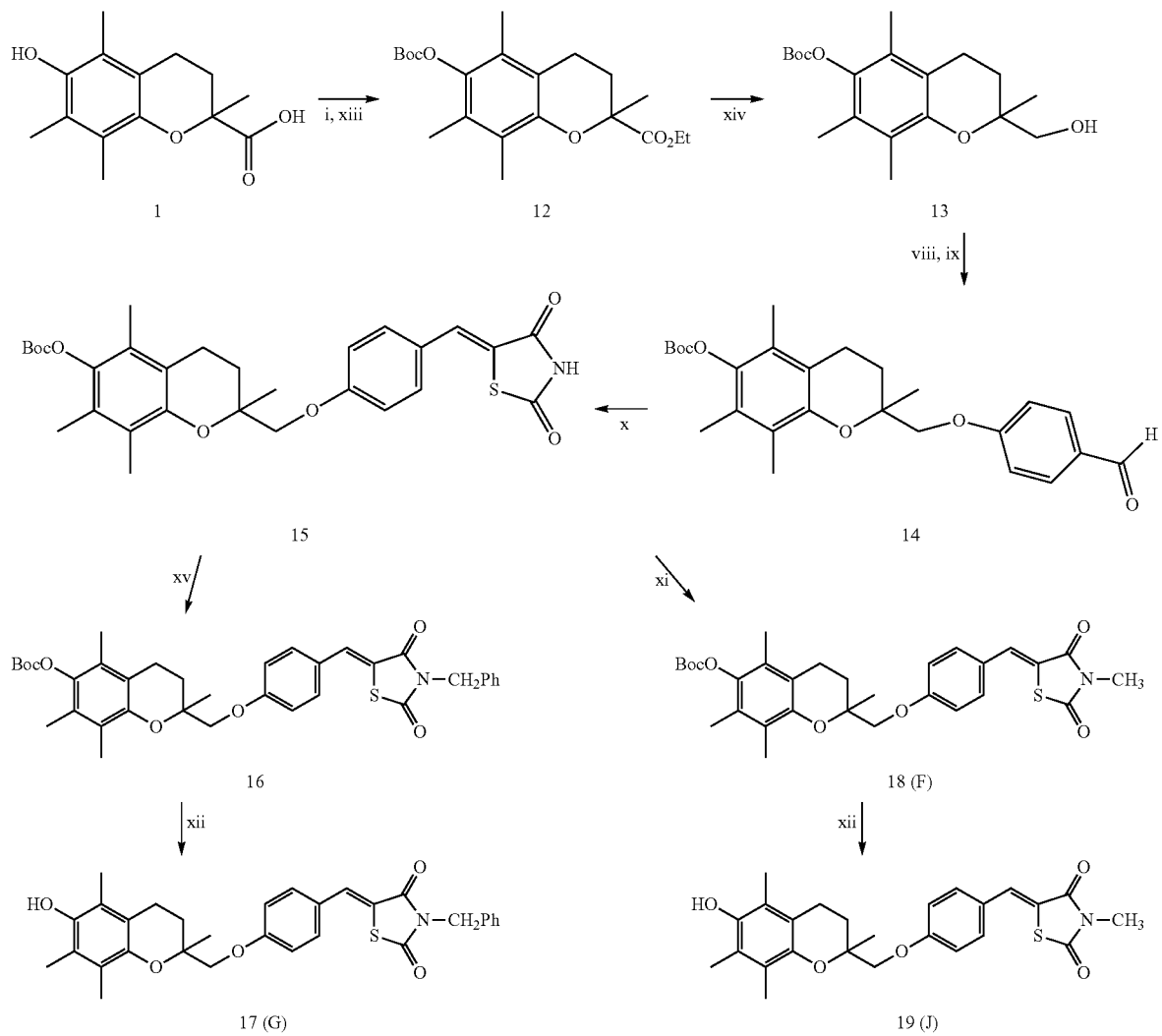

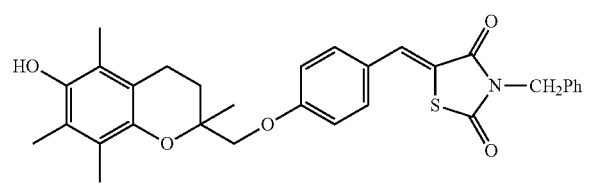

Step i: Trolox® is esterified like for the synthesis of compound C.

Step xiii: to a solution of Trolox® ethyl ester (4.72 g; 16.96 mmol) in CH$_2$Cl$_2$ (40 mL) is added di-tertbutyl dicarbonate (4.08 g; 18.96 mmol) and 4,4-dimethylaminopyridine (207 mg; 1.69 mmol) under an argon atmosphere. The solution is stirred at room temperature for 2 hours and the solvent is evaporated. The residue is dissolved in AcOEt (100 mL), the solution is washed with a 1:1 mixture of saturated NACl solution and of 1N aqueous HCl solution (60 mL), and then an aqueous NaHCO$_3$ saturated solution (2×40 mL). The organic phase is dried (MgSO$_4$) and the solvent is evaporated. The residue is purified by silica column chromatography (hexane/AcOEt, 90:10) in order to obtain the compound 12 ((±) ethyl 6-tert-butoxycarbonyloxy-2,5,7,8-tetramethylchroman-2-carboxylate) in the form of a colorless liquid (6.39 g: 16.88 mmol, yield 99%).

Step xiv: to a suspension of LiAlH$_4$ (558 mg; 14.70 mmol) in dry THF (15 mL) and at 0° C., is slowly added under argon a solution of compound 12 (6.34 g; 16.75 mmol) in dry THF (40 mL). The suspension is stirred for 1 hour (not for a longer time, in order to avoid reduction of the protective carbonate group) at 0° C., and is then brought back to room temperature. The mixture is poured into a saturated NH₄Cl solution (60 mL) and extracted with AcOEt (3×30 mL). The organic phases are collected and then washed with water (1×60 mL), with a saturated NaCl solution (1×60 mL), dried (MgSO₄) and then the solvent is evaporated in vacuo. The residue is purified by silica column chromatography (hexane/AcOEt, 80:20) in order to obtain a colorless gum which is dissolved in hexane. The evaporation of the solvent gives the compound 13 ((±) tertiobutyl 2-hydroxymethyl-2,5,7,8-tertramethylchroman-6-yl) carbonate) in the form of a white solid (5.14 g; 15.28 mmol, yield 91%).

Steps viii, ix and x: they are carried out on compound 13 in a similar way to the synthesis of compound C. The compound 14 ((±) tertiobutyl(2-(4-formylphenoxymethyl)-2,5,7,8-tetramethylchroman-6-yl)carbonate) is obtained with a yield of 86% and the compound 15 ((±) tertiobutyl (2-{4-[2-4-dioxothiazolidin-(5Z)-ylidinemethyl]phenoxymethyl}-2,5,7,8-tetramethylchroman-6-yl)carbonate) is obtained with a yield of 88%.

Step xv: to a solution of the compound 15 (270 mg: 0.5 mmol) in DMF are added K₂CO₃ (90 mg; 0.65 mmol) and then benzyl bromide (65 µm; 0.55 mmol). The reaction medium is refluxed at 80° C. with a guard of CaCl₂ for 3 hours. The reaction medium is diluted with AcOEt (30 mL) and the solution is washed with water (5×10 mL), dried (with Na₂SO₄) and the solvent is evaporated in vacuo. A foam is obtained. The residue is then solubilized in 20 mL of AcOEt under hot conditions and then left at room temperature for 72 hours. The fine white crystals formed are filtered and then washed with ice-cold AcOEt (8 mL) and then with a 1:1 AcOEt/hexane mixture (2×8 mL). The compound is then dried in vacuo in order to obtain the compound 16 ((±) tertiobutyl(2-[4-benzyl2,4,dioxo-thiazolidin-5-ylidine methyl)phenoxymethyl}-2,5,7,8-tetramethylchroman-6-yl)carbonate) in the form of white crystals (266 mg: 0.422 mmol, yield 85%).

Step xii: is carried out on the compound 16 (200 mg: 0.32 mmol) in a similar way to the synthesis of compound D. After evaporation of trifluoroacetic acid, the residue is suspended in a 1:1 mixture of AcOEt and of hexane (6 mL). The obtained suspension is filtered and washed with a 4:6 mixture of AcOEt and of hexane (4 mL), and then with hexane. After drying, the compound G is obtained as a white powder (83 mg: 0.16 mmol; yield 49%). ¹H NMR (CDCl₃) δ: 1.42 (s, 3H, CH₃); 1.85-1.95 (m, 1H, 3-HaHb chromane); 2.06-2.18 (m, 1H, 3-HaHb chromane); 2.08 (s, 3H, CH₃); 2.12 (s, 3H, CH₃); 2.16 (s, 3H, CH₃); 2.65 (m, 2H, 4-H₂ chromane); 3.96, 4.04 (System AB, J=9.6 Hz, 2H, OCH₂); 4.23 (s, 1H, OH); 4.90 (s, 2H, NCH₂Ph); 7.00 (d, J=8.5 Hz, 2H, H$_{arom}$); 7.33 (m, 3H, H$_{arom}$), 7.44 (m, 4H, H$_{arom}$); 7.86 (s, 1H, ArCH=). ESI-MS (positive mode): m/z=530.32 [M+H]+. Anal. calc., for C₃₁H₃₁NO₅S (529.63): C, 70.30; H, 5.90; N, 2.65. Found: C, 70.46; H, 5.94; N, 2.74.

(±) tertiobutyl(2,5,7,8-tetramethyl-2-[4-(3-methyl-2,4-dioxo-thiazolidin-5-ylidenemethyl)-phenoxymethyl]-chroman-6-yl)carbonate (compound F)

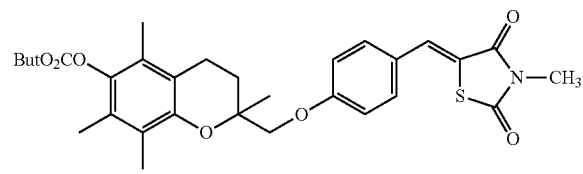

Step xi: in a similar way to the synthesis of compound 9, to a solution of compound 15 (270 mg; 0.5 mmol) in dry DMF (3 mL) are added K₂CO₃ (90 mg; 0.65 mmol) and then methyl iodide (37 µL; 0.6 mmol). The reaction medium is heated to 80° C. under argon for 4 hours. The mixture is diluted with AcOEt (30 mL), the solution is washed with a saturated NaCl solution (20 mL) and water (20 mL), dried (MgSO₄), filtered and the solvent is evacuated in vacuo in order to obtain a yellow liquid which by precipitation from cold methanol gives the compound 18 corresponding to the compound of formula F (137 mg; 0.247 mmol, yield 50%) of white crystals. 1H NMR (CDCl₃) δ: 1.43 (s, 3H, CH₃); 1.55 (s, 9H, tBu); 1.90 (m, 1H, 3-HaHb chromane); 2.04 (s, 3H, CH₃); 2.06 (s, 3H, CH₃); 2.08 (s, 3H, CH₃); 2.11 (m, 1H, 3-HaHb chromane); 2.64 (m, 2H, 4-H₂ chromane); 3.24 (s, 3H, NCH₃); 3.95; 4.05 (system AB, J=9.4 Hz, 2H, OCH2); 7.01 (d, J=8.8 Hz, 2H, H$_{arom}$), 7.46 (d, J=8.8 Hz, 2H, H$_{arom}$), 7.86 (s, 1H, H$_{arom}$). ESI-MS (positive mode): m/z=476.20 [M−Boc+H+Na]+; 520.24 [M−tBu+H+Na]+; 576.28 [M+Na]+. Anal. calc., for C₃₀H₃₅NO₇S (553.66): C, 65.08; H, 6.37; N, 2.53. Found: C, 65.10; H, 6.37; N, 2.53

(±) 5-[4-(6-Hydroxy-2,5,7,8-tetramethyl-chroman-2-ylmethoxy)-benzylidene]-3-methyl-thiazolidine-2,4-dione (compound J)

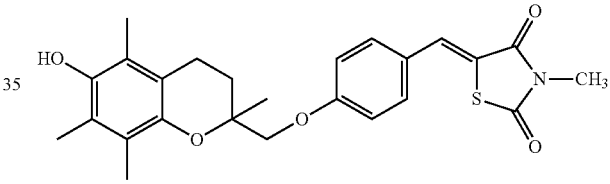

Step xii: it is carried out on the compound F in a similar way to the synthesis of compound D. A solution of the compound F (1.016 g; 2.01 mmol) in dry CH₂Cl₂ (8 mL) is cooled with an ice bath. Next trifluoroacetic acid (4 mL) is added. The reaction is left to return to room temperature and is stirred for 2 hours. The solvent is evaporated and the acid excess is removed by co-evaporation with MeOH (5 times). The obtained yellow solid is purified by silica column chromatography (hexane:AcOEt 8:2) and then precipitated from a CH₂Cl₂/Et₂O mixture in order to obtain the compound 19 corresponding to the compound of formula J in the form of a colorless solid (860 mg; 1.90 mmol, yield 94%). ¹H NMR (CDCl₃) δ: 1.42 (s, 3H, CH₃); 1.88-1.96 (m, 1H, 3-H₂ chromane); 2.08 (s, 3H, CH₃); 2.12 (s, 3H, CH₃); 2.16 (s, 3H, CH₃); 2.66 (m, 2H, 4-H₂ chromane); 3.24 (s, 3H, NCH₃); 3.96; 4.04 (system AB, J=9.3 Hz, 2H, OCH2); 7.01 (d, J=8.8 Hz, 2H, H$_{arom}$); 7.45 (d, J=8.8 Hz, 2H, H$_{arom}$); 7.87 (s, 1H, H$_{arom}$). ESI-MS (positive mode): m/z=454.03 [M+H]+; 476.00 [M+Na]+. Anal. calc., for C₂₅H₂₇NO₅S (453.54): C, 66.20; H, 6.00; N, 3.09. Found: C, 65.85; H, 6.13; N, 3.24.

Synthesis of Compound B.

Its synthesis is carried out according to the following Reaction Scheme 3:

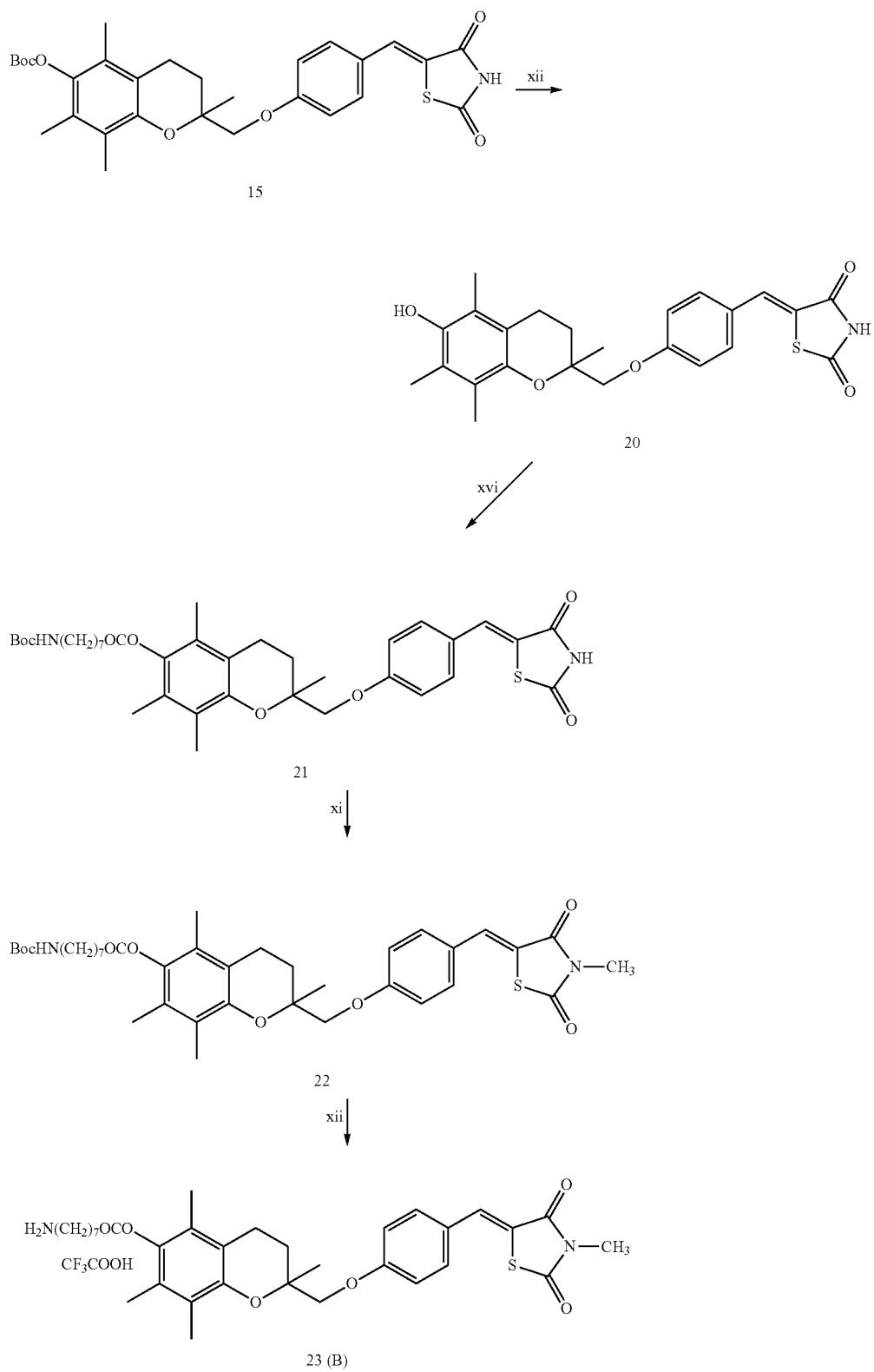
Scheme 3. Synthesis of the compound B. Reagents and conditions: xii 86% (20); xvi BocNH(CH$_2$)$_7$CO$_2$H, TEA, IBCF, and then 20, 75%; xi 85% (22); xii 59% (23 corresponding to the compound B).

(±) 8-amino {2,5,7,8-tetramethyl-2-[4-(3-methyl-2, 4-dioxo-thiazolidin-5-ylidenemethyl)-phenoxymethyl]-chroman-6-yl}octanoate trifluoroacetate (compound B)

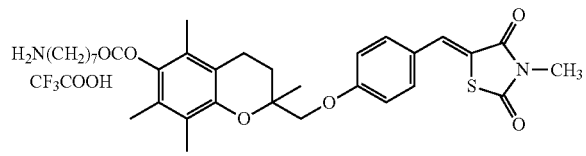

Step xii: it is carried out on the compound 15 (601 mg; 1.11 mmol) in a similar way to the synthesis of compound D. After evaporation of trifluoroacetic acid, the residue is dissolved in AcOEt (50 mL) and the solution is washed with a 5% NaHCO₃ aqueous solution (2×50 mL) and with water (2×50 mL), dried (MgSO₄) and the solvent is evaporated in vacuo. The residue is purified by silica column chromatography (hexane/AcOEt, 80:20) and then recrystallized from MeOH in order to obtain the compound 20 ((±)5-[1-[4-(6-hydroxy-2,5,7,8-tetramethylchroman-2-yl-methoxy)-phenyl]-meth-(Z)-ylidene]thiazolidine-2,4-dione) in the form of a yellow solid (422 mg; 0.95 mmol, yield 86%).

Step xvi: under a stream of argon, to a solution of 8-(tert-butoxycarbonylamino)caprylic acid (532 mg; 2.05 mmol) prepared as described by L. Guetzoyan, F. Ramiandrasoa, H. Dorizon, C. Desprez, A. Bridoux, C. Rogier, B. Pradines, M. Perrée-Fauvet, Bioorg. Med. Chem. 15 (2007) 3278-3289) in dry CH₂Cl₂ (40 mL) is added TEA (286 μL; 2.05 mmol) and the mixture is cooled with an ice bath. Next isobutyl chloroformate (266 μL; 2.05 mmol) is added and the solution is stirred for 1 hour at the same temperature, and then a solution of the compound 20 (751 mg; 1.71 mmol) and of dimethylaminopyridine (25 mg; 0.21 mmol) in CH₂Cl₂ (40 mL) is added. The mixture is stirred for 12 hours at room temperature, and then the solution is washed with an aqueous 5% NaHCO₃ solution (2×40 mL), an aqueous solution of 5% citric acid (2×40 mL) and a saturated NaCl solution (2×40 mL), dried (MgSO₄) and concentrated in vacuo. The residue is purified on silica column chromatography (CH₂Cl₂/AcOEt, 95:5) by using the <<Axxial® Modul Prep>> machine (see general points) in order to obtain the compound 21 ((±)2-{4-[2,4-dioxo-thiazolidin-(5Z)-ylidenemethyl]-phenoxymethyl}-2,5,7,8-tetramethyl-chroman-6-yl 8-tert-butoxycarbonylamino-octanoate) in the form of an amorphous yellow solid (873 mg; 1.28 mmol; yield 75%).

Step xi: the reaction is conducted on the compound 21 in a similar way to the one carried out for obtaining the compound 18 corresponding to compound F: To a solution of the compound 21 (259 mg; 0.38 mmol) in dry DMF (4 mL) are added K₂CO₃ (68 mg; 0.49 mmol) and CH₃I (28 μL; 0.45 mmol). The mixture is stirred under argon at 80° C. for 4 hours, and is then diluted with AcOEt (30 mL). The solution is washed with a saturated NaCl solution (20 mL) and with water (20 mL), dried (MgSO₄), filtered and the solvent is evaporated. The residue (yellow oil) is purified by precipitation from cold MeOH in order to obtain compound 22 (2,5,7,8-tetramethyl-2-[4-(3-methyl-2,4-dioxo-thiazolidin-5-ylidene-methyl)-phenoxymethyl]-chroman-6-yl 8-tert-butoxycarbonylamino-octanoate) in the form of a colorless solid (223 mg; 0.32 mmol; yield 85%)

Step xii: it is carried out on compound 22 in a similar way to the synthesis of compound D: A solution of the compound 22 (157 mg; 0.226 mmol) in dry CH₂Cl₂ (2 mL) is cooled in ice, and then some trifluoroacetic acid (1 mL) is added with stirring. The solution is left to return to room temperature and stirred for 3 hours. The solvent is evaporated and the excess acid is removed by co-evaporation with MeOH (5 times). The obtained yellow solid is washed with Et₂O in order to obtain compound 23 (compound B) as an off-white solid (95 mg; 0.134 mmol, yield 59%). ¹H NMR (CDCl₃) δ: 1.29-1.40 (m, 4H, CH₂<<linker>>); 1.42 (s, 3H, CH₃); 1.55-1.83 (m, 4H, CH₂<<linker>>); 1.84-1.94 (m, 1H, 3-HaHb chromane); 1.95 (s, 3H, ArCH₃); 1.99 (s, 3H, ArCH₃); 2.05 (s, 3H, ArCH₃); 2.00-2.24 (m, 3H, 3-HaHb chromane, CH2<<linker>>); 2.50-2.70 (m, 4H, 4-H2 chromane, CH₂<<linker>>); 2.79-2.97 (m, 2H, CH₂<<linker>>); 3.23 (s, 3H, NCH₃); 3.95, 4.05 (system AB, J=9.3 Hz, 2H, CH₂O); 7.00 (d, J=8.7 Hz, 2H, H_{arom}); 7.44 (d, J=8.7 Hz, 2H, H_{arom}); 7.85 (sl, 2H, NH₂); 7.85 (s, 1H, ArCH=). ESI-MS (positive mode): m/z=595.14 [M+H]⁺. Anal. calc., for C₃₅H₄₃F₃N₂O₈S (708.8): C, 59.31; H, 6.11; N, 3.95. Found: 58.83; H, 6.06; N, 3.81.

Synthesis of Compound A.

Its synthesis is carried out according to the following reaction scheme 4:

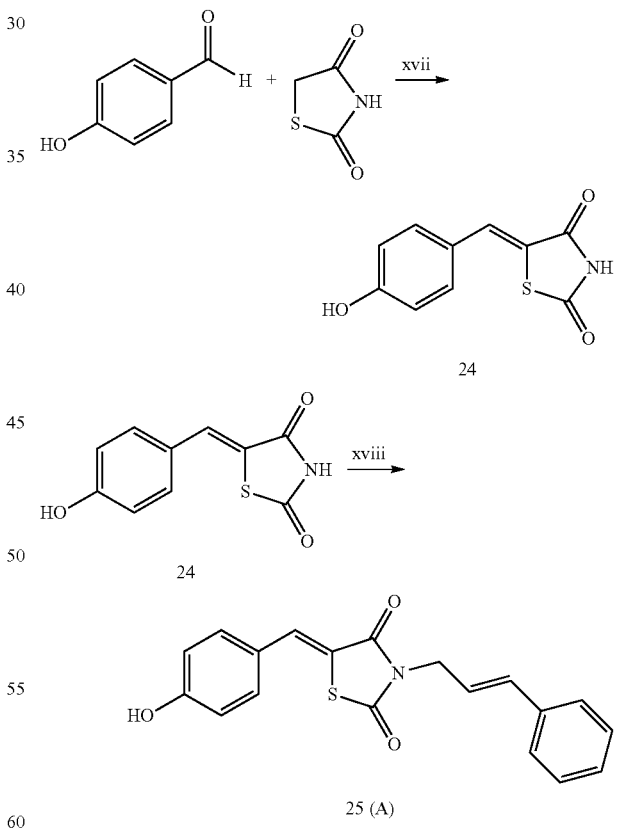

Scheme 4. Synthesis of compound A. Reagents and conditions: xvii AcOH, (β-alanine, 77%; xviii cinnamyl bromide K₂CO₃, 29%.

5-(4-hydroxy-benzylidene)-3-(3-phenyl-allyl)-thiazolidine-2,4-dione (compound A)

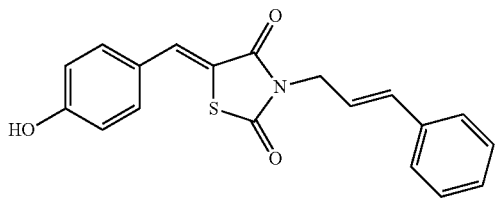 [SMILES: O=C1S/C(=C\c2ccc(O)cc2)C(=O)N1C/C=C/c1ccccc1]

Step xvii: 4-hydroxybenzaldehyde and 2,4-thiazolidinedione are condensed in acetic acid in the presence of β-alanine according to the conditions described in the literature (Y. Luo, L. Ma, H. Zheng, L. Chen, R. Li, C. He, S. Yang, X. Ye, Z. Chen, Z. Li, Y. Gao, J. Han, G. He, L. Yang, Y. Wei, J. Med. Chem 53 (2010) 273-281) in order to obtain compound 24 (5-(4-hydroxybenzylidene)thiazolidine-2,4-dione).

Step xviii: a suspension of compound 24 (305 mg; 1.38 mmol), cinnamyl bromide (287 mg; 1.51 mmol) and K$_2$CO$_3$ (247 mg; 1.79 mmol) in dry DMF (6 mL) is stirred at 80° C. for 12 hours. The mixture is diluted with AcOEt (30 mL), the solution is washed with water (3×20 mL), dried (MgSO$_4$), filtered and the solvent is evaporated in vacuo in order to obtain a yellow liquid, subsequently purified by precipitation from CH$_2$Cl$_2$ in order to obtain the compound A (137 mg; 0.41 mmol, yield 29%) in the form of a colorless solid. $^1$H NMR (DMSO) δ: 4.43 (d, J=5.6 Hz, 2H, —CH$_2$); 6.23-6.37 (m, 1 H, —CH═); 6.60 (d, J=16.0 Hz, 1H, —CH═); 6.95 (d, J=8.5 Hz, 2H, H$_{arom}$), 7.19-7.40 (m, 3H, H$_{arom}$), 7.41-7.59 (m, 4H, H$_{arom}$), 7.88 (5, 1H, ArCH═); 10.37 (br s, 1H, —OH). ESI-MS (negative mode): m/z=336.07 [M–H]$^-$. Anal. calc., for C$_{19}$H$_{15}$NO$_3$S (337.4): C, 67.64; H, 4.48; N, 4.15. Found: C, 67.25; H, 4.55; N, 4.03.

Synthesis of compound H

Its synthesis is carried out according to the following reaction scheme 5:

Scheme 5. Synthesis of compound H.

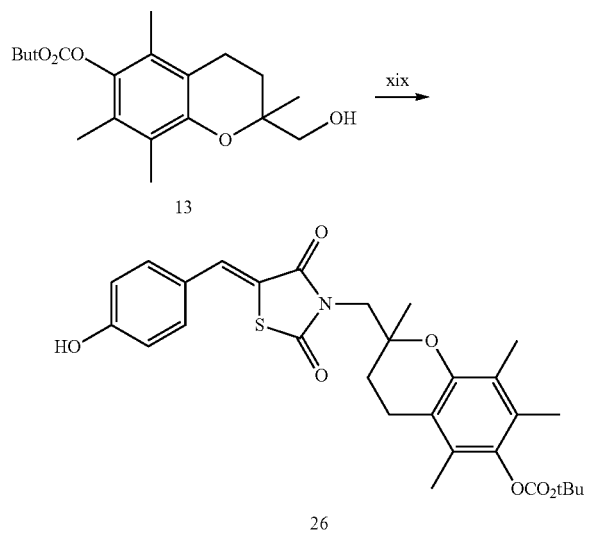

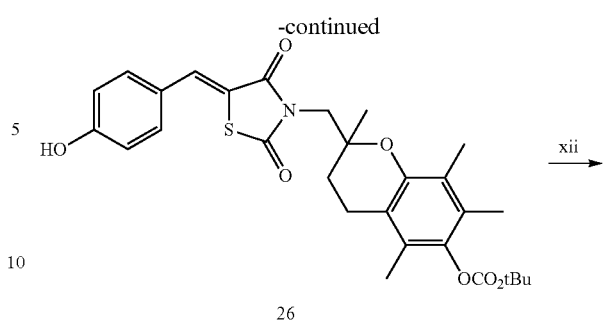

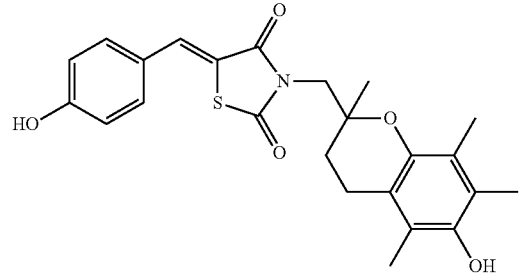 [SMILES: Cc1c(C)c2c(c(C)c1O)CCC(C)(CN1C(=O)S/C(=C\c3ccc(O)cc3)C1=O)O2]

27 (H)

Reagents and conditions: xix Tf$_2$O, Pyr. quant, and then 24, K$_2$CO$_3$, 42%; xii 90% (27, compound H).

(±) 5-(4-hydroxy-benzylidene)-3-(6-hydroxy-2,5,7,8-tetramethyl-chroman-2-ylmethyl)-thiazolidine-2,4-dione (compound H)

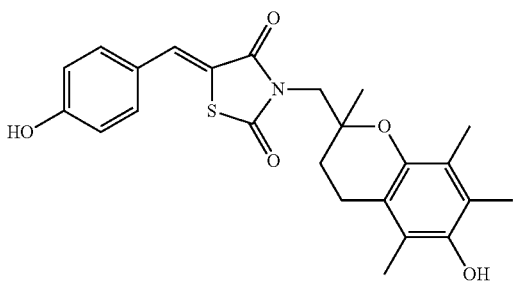

Step xix: a solution of anhydrous pyridine (1.036 mL; 12.80 mmol) in dry CH$_2$Cl$_2$ (10 mL) under argon is cooled to 0° C., and trifluoromethanesulfonic anhydride (522 µL; 3.15 mmol) is then added dropwise. A solution of the compound 13 (730 mg; 2.17 mmol) in dry CH$_2$Cl$_2$ (5 mL) is added to the mixture. The solution is stirred at 0° C. for 30 mins and the solvent is evaporated. The excess pyridine is co-evaporated twice with toluene and the residue is dissolved in AcOEt (25 mL). The organic phase is washed with an aqueous 5% NaHCO$_3$ solution (2×30 mL) and a saturated NaCl solution (2×30 mL), dried (MgSO$_4$), filtered and the solvent is evaporated in order to obtain the desired triflate in the form of a yellow liquid directly used in the subsequent step. To a solution of the previous triflate in dry DMF (6 mL) are added the compound 24 (456 mg; 2.06 mmol) and K$_2$CO$_3$ (470 mg; 2.97 mmol). The mixture is stirred under argon at room temperature for 24 hours and then diluted in AcOEt (50 mL). The organic phase is washed with water (5×30 mL), dried (MgSO$_4$), filtered and the solvent is evaporated in order to obtain an orange foam which is then purified by silica column chromatography (hexane:AcOEt 9:1 and then 8:2) in order to obtain a yellow solid which is suspended in 10 mL of hexane:AcOEt 8:2 mixture. The suspension is sonicated, and then filtered and washed with the same solvent mixture in order to obtain after drying, the compound 26 (tertiobutyl {2-[5-(4-hydroxy-benzylidene)-2,4-dioxo-thiazolidin-3-ylmethyl]-2,5,7,8-tetramethyl-chroman-6-yl}carbonate) in the form of a white solid (462 mg; 0.86 mmol; yield 42%).

Step xii: in a similar way to the synthesis of compound D: To a suspension of compound 26 (300 mg; 0.56 mmol) in CH$_2$Cl$_2$ (8 mL) is added trifluoroacetic acid (2 mL); the solution is stirred for 1 hour and the solvent is then dry evaporated. The residue is dissolved in AcOEt (30 mL) and the solution is then washed with a solution of 5% NaHCO$_3$ (10 mL) and then with water (2×1 0 mL). The solvent is evaporated in vacuo in order to obtain a yellow liquid which is stored at 4° C. for 48 h. The obtained yellow crystals are suspended in Et$_2$O (10 mL), filtered, washed with Et$_2$O (2×5 mL) and then with hexane (2×5 mL) in order to obtain after drying the compound 27 (compound H) in the form of yellow crystals (221 mg; 0.50 mmol; yield 90%). $^1$H NMR (DMSO) δ: 1.14 (s, 3H, CH$_3$); 1.78 (m, 2H, 3-H$_2$ chromane); 1.92 (s, 3H, ArCH$_3$); 2.01 (s, 3H, ArCH$_3$); 2.03 (s, 3H, ArCH$_3$); 2.59 (m, 2H, 4-H$_2$ chromane); 3.85 (s, 2H, CH$_2$O); 6.92 (d, J=8.6 Hz, 2H, H$_{arom}$), 7.40 (s, 1H, OH); 7.50 (d, J=8.6 Hz, 2H, H$_{arom}$); 7.85 (s, 1H, ArCH=); 10.33 (s, 1H, OH). ESI-MS (mode positif): m/z=440.06 [M+H]$^+$, 462.03 [M+Na]$^+$, 478.08 [M+K]$^+$. Anal. calc., for C$_{24}$H$_{25}$NO$_5$S (439.52): C, 65.58; H, 5.73; N, 3.19. Found: 65.13; H, 5.85; N, 3.28.

Synthesis of Compound Q

Its synthesis is carried out according to the following reaction scheme 6:

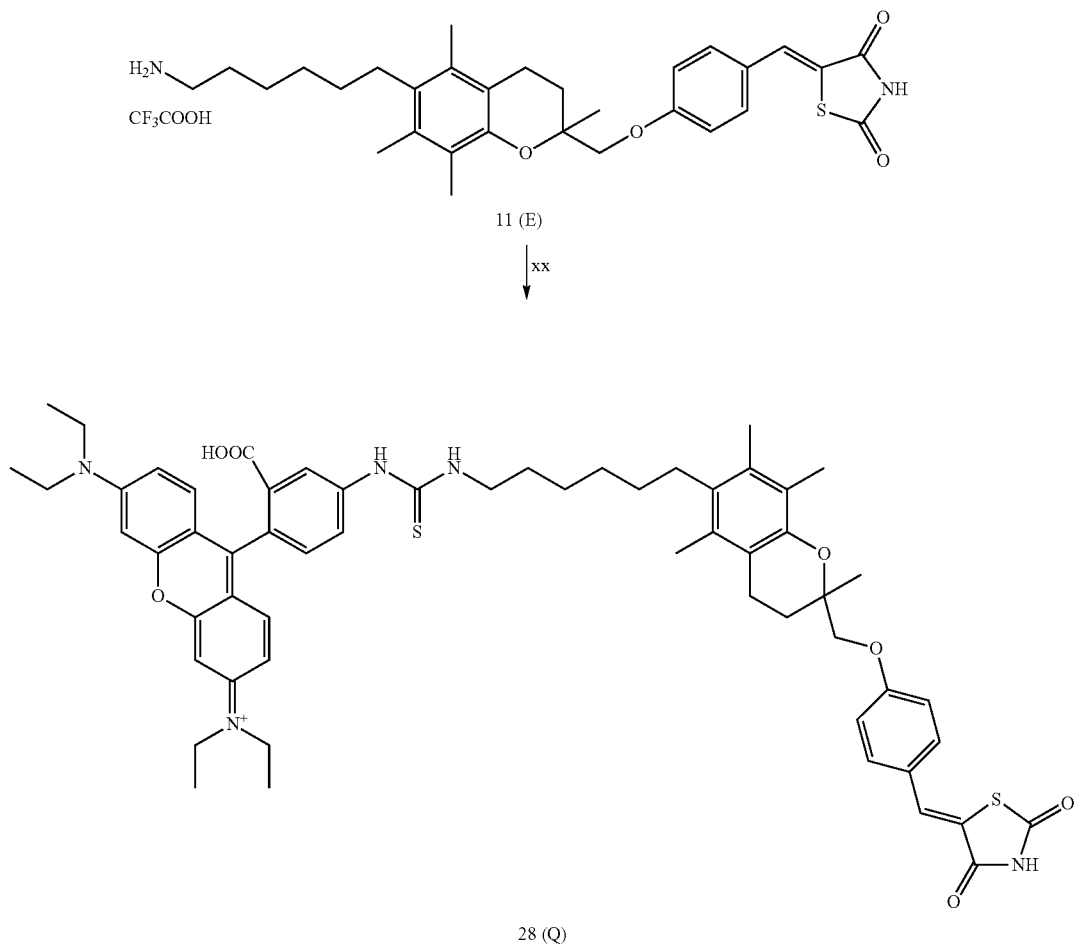

Scheme 6. Synthesis of compound Q. Reagents and conditions: xx TEA, RhodamineB-isothiocyanate 57%.

(±) (9-{2-carboxy-4-[3-(6-{2-[4-(2,4-dioxo-thiazoli-din-5-ylidenemethyl)-phenoxy-methyl]-2,5,7,8-te-tramethyl-chroman-6-yl}-hexyl)-thioureido]-phe-nyl}-6-diethylamino-xanthen-3-ylidene)-diethyl-ammonium (compound Q)

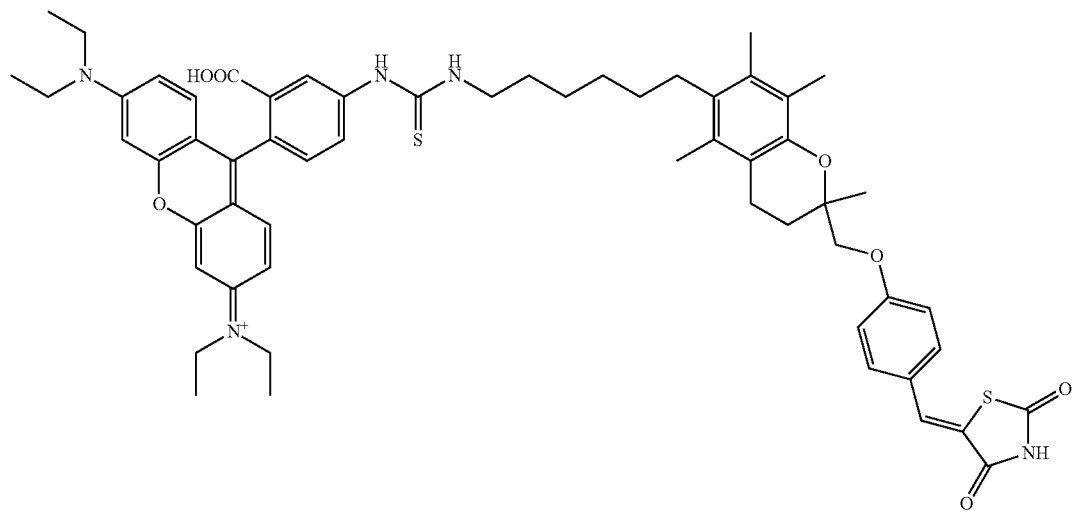 [SMILES: CCN(CC)c1ccc2c(-c3ccc(NC(=S)NCCCCCCc4c(C)c(C)c5c(c4C)CCC(C)(COc4ccc(/C=C6\SC(=O)NC6=O)cc4)O5)cc3C(=O)O)c3ccc(=[N+](CC)CC)cc-3oc2c1]

Step xx: To a solution of the compound E pose E (23 mg; 36 μmol) in dry EtOH (1 mL) is added triethylamine (2.2 mL; 54.2 (μmol). The resulting precipitate is dissolved by adding dichloromethane (0.2 mL). To this solution is added rhodamine B-isothiocyanate (19.4 mg; 36.1 μmol) and the reaction medium is stirred at room temperature in darkness for 4 days. The solvent is evaporated in vacuo and the crude residue is purified by silica column chromatography in order to obtain the compound 28 (compound Q) in the form of a red solid (21 mg; 20.5 μmol; yield 57%). ESI-MS (high resolution, positive mode): m/z=calculated: 1022.4555; measured: 1022.4584 [M]+.

EXAMPLES

Hepatic Toxicity

Hepatocyte viability was measured for different compounds according to the invention with cryopreserved human hepatocytes (primary culture) suspended and distributed in 96-well plates with a density of $0.1 \times 10^6$ cells per well, in a 50 μm culture medium per well (DMEM+gentamycin (50 mg/L)+insulin (4 mg/L)+dexamethasone (1 μM)) in a $CO_2$/air (5%/95%) humidified atmosphere at 37° C. After 30 minutes for attaining equilibrium, 50 μM of culture medium containing the tested compounds (dissolved in DMSO) or of medium only containing DMSO (final concentration of 0.1%) were added with stirring at 900 rpm.

Cytotoxicity is evaluated with an MTT (Thiazolyl Blue Tetrazolium Bromide) test. The tested compounds or the DMSO are left to incubate for 90 minutes, and then 10 μL of MTT at 10 mg/10 mL are added per well for 30 mins. Next, the plates are centrifuged for 10 minutes at 2,000 g, the MTT is removed and some DMSO is added in an amount of 100 μL per well. The plates are gently shaked and then absorbance is measured at 595 nm by means of a spectrophotometric reader of micro-plates. The hepatocyte viability measured here corresponds to the percentage of surviving hepatocytes after 90 minutes of incubation with the compounds tested at a concentration of 100 μM, relatively to non treated cells.

The same tests were conducted for a concentration of compounds at 200 μM.

As a comparison, the hepatocytes viability is also measured for troglitazone (compound K).

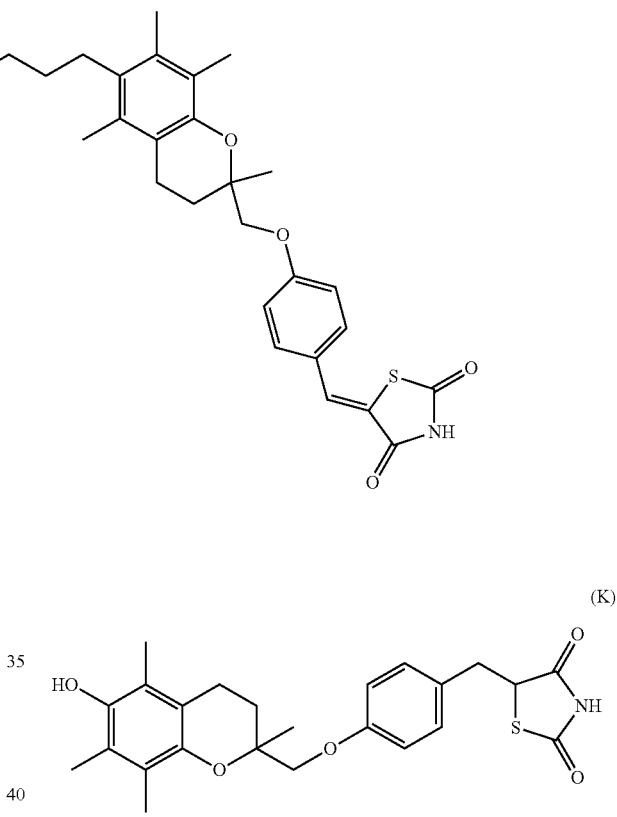

and a compound of formula L described by Chen. et. al. in patent application WO 2009/105621:

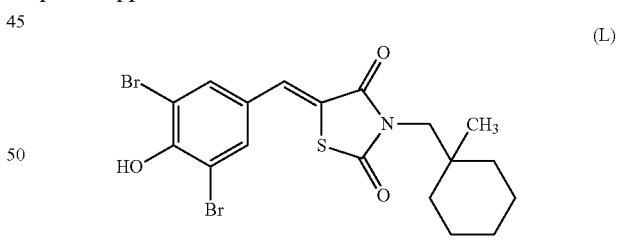

The tests were conducted in two distinct campaigns. In both cases, troglitazone (K) was used as a reference molecule.

The results of the two campaigns are indicated in Tables I and II below:

TABLE I

| Compound | Hepatocyte viability % (100 μM) | Hepatocyte viability % (200 μM) |
|---|---|---|
| A | 89 | 63 |
| C | 85 | 80 |
| D | 83 | 83 |

TABLE I-continued

| Compound | Hepatocyte viability % (100 μM) | Hepatocyte viability % (200 μM) |
|---|---|---|
| E | 83 | 80 |
| K (comp.) | 79 | 30 |
| L (comp.) | 42 | 30 |

TABLE II

| Compound | Hepatocyte viability % (100 μM) | Hepatocyte viability % (200 μM) |
|---|---|---|
| F | 81 | 66 |
| G | 87 | 63 |
| H | 110 | 103 |
| J | 120 | 120 |
| K (comp.) | 52 | 22 |

The results above show that the compounds according to the invention have at 100 μM at 200 μM, hepatocyte viability greater than 50%, or even greater than 60% or even greater than 80%, and even greater than 85%, while the comparative compound described by Chen. et. al. has hepatocyte viability of only 42% at 100 μM and of 30% at 200 μM, and troglitazone has hepatocyte viability of only 30% at 200 μM.

Tests on Mice

A toxicity test was conducted on mice for the molecules D and E. These molecules therefore only differ by the substituted methyl group on thiazolidinedione. As a comparison, the test was also conducted by using Δ2TGZ. These analyses were conducted on female NMRI mice weighing 20-25 g. Groups of three mice were set up: a non-injected control batch, a batch receiving the solvent of the molecules to be tested (water PPI, polyethylene glycol 400, absolute ethanol mixture in proportions 5/3/2), three other batches receiving the molecules to be tested. The compounds were injected into the tail vein of mice anaesthetized beforehand. The animals were weighed before and then 24 hours and 48 hours after intravenous injection of the products at the different tested doses and then they were also weighed three times a week for two weeks. The behavior of the whole of the mice was observed before, and then one hour, two hours and three hours after the intravenous injection and then daily for two weeks. The compounds were first tested at the limit of their solubility. Depending on the obtained results (mortality, weight loss, change in behavior, smaller doses were used in order to specifically determine the tolerated maximum dose. When less than 50% mortality was observed or when less than 50% of the animals had a weight loss greater than 25% or less than 50% of the animals had behavioral modifications, the dose of the compound was considered as non-toxic (MTD).

The maximum tolerated dose of D is 65.5 mg/kg, and 34 mg/kg for E. The result for Δ2TGZ is less than 34 mg/kg.

This shows the protective effect related to the presence of the methyl group on thiazolidinedione since D and E only differ by this group.

Antiproliferative Activity

Antiproliferative activity was measured for different compounds according to the invention by analysis of cytoxicity at $10^{-5}$ M on diverse cancer cell lines in DMSO in triplicate. For certain molecules and certain lines, the same procedure was used for determining the IC50 values (the required concentration in μM for inhibiting by half the proliferation of the cells), by conducting cytotoxicity tests at concentrations from 0.005 μM to 100 μM in duplicate. The procedure is the following. The cells of the relevant line are sown in the suitable medium (see Table III) added with L-glutamine, with 10% (v/v) of fetal calf serum, 100 IU of penicillin, 100 μg/mL of streptomycin and 1.5 μg/mL of fungizone and maintained under 5% of $CO_2$ at 37° C. 96-well plates are sown with the required number of cells per well (see Table III) in 200 μL of medium. 24 hours later, the chemical compounds to be investigated, dissolved in DMSO, are added and the media are maintained for 72 hours under these conditions with a set final concentration in DMSO (1%). The controls received an equal volume of DMSO. The number of viable cells is measured at 490 nm with the MTS reagent (Promega, Madison Wis.). The IC50s are calculated as the concentrations of compounds inducing 50% inhibition of cell proliferation.

TABLE III

| Cell line | Number of cells per well | Culture medium |
|---|---|---|
| MCF7 | 1,900 | RPMI |
| HCT116 | 1,800 | RPMI |
| MDA231 | 1,300 | RPMI |
| MDA435 | 1,000 | RPMI |
| Mia-PaCa | 1,200 | DMEM |
| HepG2 | 8,000 | DMEM |
| PC3 | 2,500 | RPMI |
| LNCaP | 5,000 | RPMI |

As a comparison, the tests were also conducted with troglitazone (compound K) and the compound of formula L described by Chen et al. in patent application WO 2009/105621 defined above.

Tables IV and V below indicate the percentage of inhibition of cell growth, i.e. the percentage of dead cells after treatment with a compound dose of $10^{-5}$ M. The tests were conducted in triplicate.

TABLE IV

| Compound | MCF7 | HCT116 | MDA231 | MDA435 |
|---|---|---|---|---|
| A | 65 | 83 | 91 | 82 |
| B | 101 | 99 | 101 | 100 |
| C | 24 | 55 | 51 | 39 |
| D | 101 | 101 | 101 | 101 |
| E | 97 | 93 | 92 | 65 |
| H | 95 | 95 | 95 | 87 |
| J | 0 | 32 | 36 | 5 |
| Q | 59 | 80 | 71 | 59 |
| K (comp.) | 3 | 9 | 12 | 12 |
| L (comp.) | 76 | 87 | 53 | 69 |

TABLE V

| Compound | Mia-PaCa | HepG2 | PC3 | LNCaP |
|---|---|---|---|---|
| A | 84 | 59 | 43 | 37 |
| B | 101 | 92 | 98 | 91 |
| C | 30 | 77 | 26 | 68 |
| D | 103 | 100 | 92 | 88 |
| E | 94 | 87 | 40 | 53 |
| H | 102 | 79 | 64 | 51 |
| J | 20 | 40 | 14 | 33 |
| Q | 70 | 75 | 60 | 67 |
| K (comp.) | 2 | 14 | 14 | 17 |
| L (comp.) | 65 | 74 | 47 | 81 |

Tables IV and V above show that the compounds according to the invention have much greater antiproliferative activity than that of troglitazone. Moreover, the results allow confirmation that the compound L described by Chen et al. is quite active on all the lines, but a little less than the most active of the compounds according to the invention.

As an indication, the measured IC50s (µM) of a few of the previous compounds on a few cancer lines are indicated in Table VI

TABLE VI

| Compound | MCF7 | MDA231 | Mia-PaCa | HepG2 | LNCaP |
|---|---|---|---|---|---|
| A | 5.2 | 2.2 | 4.8 | 10.1 | 19.4 |
| B | 0.9 | 0.2 | 0.6 | 1.0 | 1.0 |
| C | 9.6 | 2.1 | 8.8 | 2.4 | 6.4 |
| D | 6.9 | 4.6 | 3.2 | 7.9 | 6.5 |
| E | 6.4 | 4.7 | 3.9 | 3.1 | 5.1 |
| H | 3.4 | 1.9 | 1.3 | 5.7 | 6.1 |
| J | 52.6 | 4.9 | 24.5 | 20.4 | 17.4 |
| L (comp.) | 9.3 | 5.7 | 8.1 | 8.8 | 1.8 |

The indicated values are the averages of two independent values. It will be noted that molecule J has a particular characteristic, i.e. it is active on non-hormono-dependent breast cancer cells (MDA-231), and is inactive on hormono-dependent breast cancer cells (MCF-7).

Thus, these results show that unlike the compounds developed in the prior art, the novel compounds according to the present invention are not toxic on hepatocytes, while retaining good properties of antiproliferative activity.

The invention claimed is:

1. A compound of formula (I)

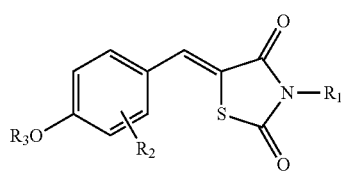

(I)

having, at a concentration of 100 µM, hepatocyte viability greater than 60% corresponding to the percentage of surviving suspended human hepatocytes after 90 minutes of incubation and,
wherein $R_3$ is a group:

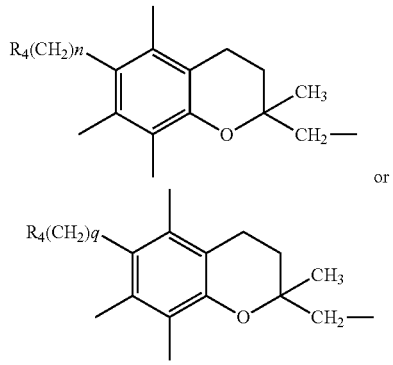

or where n and q are greater than 1, and $R_4$ and $R_8$ are respectively selected from the group consisting of OH, COOR, NRR', NHCOOR", and NHM, R and R' being selected from the group consisting of H, an alkyl and a benzyl group, R" being selected from the group consisting of an alkyl group and a benzyl group and M being a fluorescent group, $R_1$ is selected from the group consisting of H, an alkyl, benzyl, —(CH$_2$)$_m$—CH═CH-Φ, and

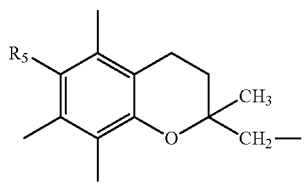

group, where m is greater than or equal to 1, $R_5$ is selected from the group consisting of H, OH, COOR, OCOOR, (CH$_2$)$_p$R$_9$, O(CH$_2$)$_p$R$_9$, and OCO(CH$_2$)$_p$R$_9$, where p is greater than 1, $R_9$ being selected from the group consisting of H, OH, COOR, NRR', NHCOOR", and NHM, R and R' being selected from group consisting of the group consisting of H, an alkyl and a benzyl group, R" being selected from the group consisting of an alkyl and a benzyl group and M being a fluorescent group, $R_2$ is a hydrogen atom or a substituent group selected from the group consisting of a amino, methoxy, ethoxy, nitro, phenyl, alkyl, and hydroxyl, when $R_1$ is an alkyl or benzyl group, $R_2$ is a hydrogen atom or a substituent group selected from the group consisting of halo, amino, methoxy, ethoxy, nitro, phenyl, alkyl, trifluoromethyl, and hydroxyl, when $R_1$ is selected from the group consisting of H, —(CH$_2$) m-CH═CH-Φ, and

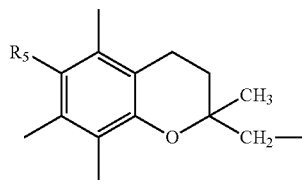

2. The compound according to claim 1, wherein $R_1$ is H and $R_4$ is NRR', R and R' being selected from the group consisting of H, an alkyl group and a benzyl group.

3. The compound according to claim 2 of formula E:

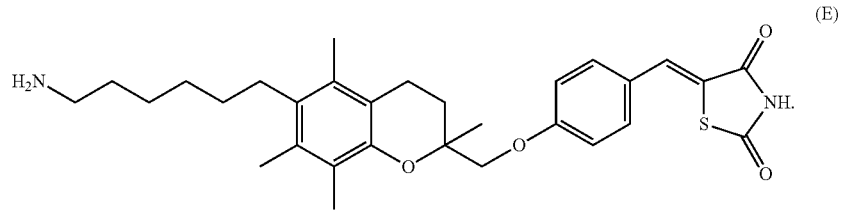 [SMILES: Cc1c(C)c2c(c(C)c1CCCCCCN)CCC(C)(COc1ccc(/C=C3\SC(=O)NC3=O)cc1)O2]

(E)

4. The compound according to claim 1, wherein $R_1$ is H and $R_4$ is NHCOOR", R" being selected from the group consisting of an alkyl and a benzyl group.

5. The compound according to claim 4 of formula C:

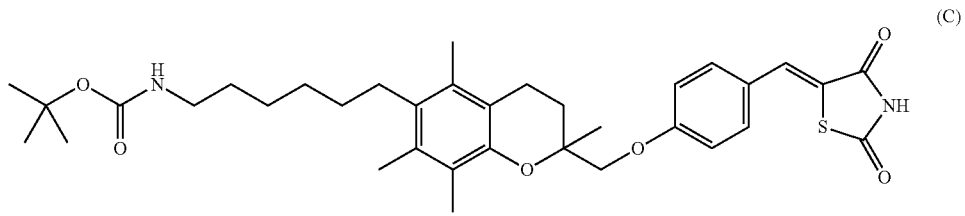

6. The compound according to claim 1, wherein $R_1$ is an alkyl group and $R_3$ is a group

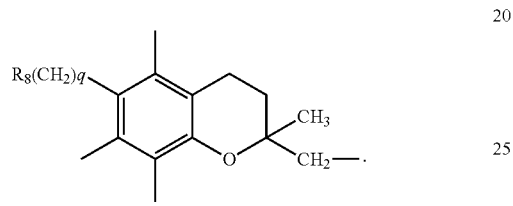

7. The compound according to claim 6, wherein $R_1$ is an alkyl group and $R_8$ is an NRR' group, R and R' being selected from H, an alkyl and a benzyl group.

8. The compound according to claim 7 of formula D:

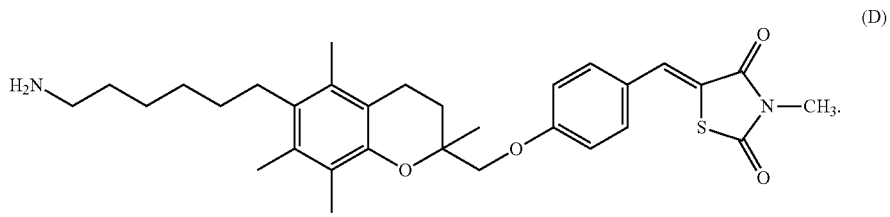 [SMILES: Cc1c(C)c2c(c(C)c1CCCCCCN)CCC(C)(COc1ccc(/C=C3\SC(=O)N(C)C3=O)cc1)O2]

9. A pharmaceutical composition, comprising as an active ingredient at least one compound of formula (I) according to claim 1 with pharmaceutically acceptable mineral and organic acids or with pharmaceutically acceptable mineral or organic bases.

10. The pharmaceutical composition according to claim 9, wherein the active ingredient is mixed with at least one of the compounds selected from at least one pharmaceutically acceptable excipient and at least one other active ingredient.

* * * * *